United States Patent
Greeley et al.

(10) Patent No.: US 10,736,618 B2
(45) Date of Patent: Aug. 11, 2020

(54) MODULAR LIGHTED SURGICAL RETRACTOR

(71) Applicant: Medtronic Advanced Energy LLC, Minneapolis, MN (US)

(72) Inventors: Roger D. Greeley, Portsmouth, NH (US); Jonathan J. Barry, Stratham, NH (US); David Hubelbank, Litchfield, NH (US); Ryan Kelley, Denver, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 27 days.

(21) Appl. No.: 15/863,049

(22) Filed: Jan. 5, 2018

(65) Prior Publication Data

US 2018/0206832 A1 Jul. 26, 2018

Related U.S. Application Data

(60) Provisional application No. 62/449,650, filed on Jan. 24, 2017.

(51) Int. Cl.
*A61B 17/02* (2006.01)
*A61B 90/30* (2016.01)
(Continued)

(52) U.S. Cl.
CPC ............... *A61B 17/02* (2013.01); *A61B 1/06* (2013.01); *A61B 1/32* (2013.01); *A61B 90/30* (2016.02);
(Continued)

(58) Field of Classification Search
CPC ........... A61B 90/36; A61B 1/32; A61B 90/30; A61B 1/06; A61B 17/02; A61B 2017/0046
See application file for complete search history.

(56) References Cited

U.S. PATENT DOCUMENTS

| 4,344,419 A | 8/1982 | Burgin |
| 4,638,792 A * | 1/1987 | Burgin ..................... A61B 1/24 600/184 |

(Continued)

FOREIGN PATENT DOCUMENTS

| CN | 105559740 A | 5/2016 |
| WO | 2004044632 A1 | 5/2004 |
| WO | 2013/044151 A1 | 3/2013 |

OTHER PUBLICATIONS

PCT Search Report and Written Opinion dated Mar. 15, 2018 for PCT/US2018/012515 (12 pages).

(Continued)

*Primary Examiner* — Ellen C Hammond
*Assistant Examiner* — Tara Rose E Carter
(74) *Attorney, Agent, or Firm* — Dicke, Billig & Czaja, PLLC

(57) ABSTRACT

A modular surgical retractor including a handle and a blade. The handle includes a base and a neck. The neck projects from an end of the base to a tail region. The blade includes a head section and a blade member. The head section includes opposing side walls and a floor combining to define a slot sized to receive the neck. The blade member projects from the head section. The blade is removably attached to the handle. In an attached state, an attachment face of each side wall contacts the end of the base, and the floor contacts the tail region. In some embodiments, a light source, such as an LED, is disposed within the neck and arranged to emit light along a face of the blade member. Two or more additional blades are provided, each additional blade including the head section and a differently configured blade member.

20 Claims, 19 Drawing Sheets

(51) Int. Cl.
 *A61B 1/06* (2006.01)
 *A61B 1/32* (2006.01)
 *A61B 90/00* (2016.01)
 *A61B 17/00* (2006.01)

(52) U.S. Cl.
 CPC ...... *A61B 90/36* (2016.02); *A61B 2017/0046* (2013.01); *A61B 2017/00473* (2013.01); *A61B 2017/00734* (2013.01)

(56) References Cited

U.S. PATENT DOCUMENTS

| | | |
|---|---|---|
| 4,697,578 A | 10/1987 | Burgin |
| 5,928,139 A | 7/1999 | Koros et al. |
| 5,947,896 A | 9/1999 | Sherts et al. |
| 5,967,971 A | 10/1999 | Bolser |
| 6,035,742 A | 3/2000 | Hollingsworth et al. |
| D425,202 S | 5/2000 | Hammond et al. |
| 6,080,105 A | 6/2000 | Spears |
| 6,109,918 A | 8/2000 | Hammond et al. |
| 6,196,968 B1 | 3/2001 | Rydin et al. |
| 6,322,499 B1 | 11/2001 | Evans et al. |
| 6,322,500 B1 | 11/2001 | Sikora et al. |
| 6,331,157 B2 | 12/2001 | Hancock |
| D453,292 S | 2/2002 | Tsuzuki |
| 6,364,832 B1 | 4/2002 | Propp |
| D461,390 S | 8/2002 | Livingston |
| 6,554,768 B1 | 4/2003 | Leonard |
| 6,729,877 B2 | 5/2004 | Rahman |
| 6,805,666 B2 | 10/2004 | Holland et al. |
| 6,817,978 B2 | 11/2004 | Holland et al. |
| 6,893,394 B2 | 5/2005 | Douglas et al. |
| 6,929,606 B2 | 8/2005 | Ritland |
| 7,306,559 B2 | 12/2007 | Williams |
| 7,384,392 B2 | 6/2008 | Bayat |
| 7,481,766 B2 | 1/2009 | Lee et al. |
| D593,716 S | 6/2009 | Strauss |
| 7,686,492 B2 | 3/2010 | Vayser et al. |
| 7,766,825 B2 | 8/2010 | Hamel |
| 7,922,658 B2 | 4/2011 | Cohen et al. |
| 8,029,440 B2 | 10/2011 | Bimkrant et al. |
| D648,204 S | 11/2011 | Parvey |
| 8,047,987 B2 | 11/2011 | Grey et al. |
| 8,062,217 B2 | 11/2011 | Boucher et al. |
| 8,088,066 B2 | 1/2012 | Grey et al. |
| 8,097,026 B2 | 1/2012 | Gorek |
| D658,288 S | 4/2012 | Ryshkus et al. |
| 8,187,180 B2 | 5/2012 | Pacey |
| 8,257,250 B2 | 9/2012 | Tenger et al. |
| 8,262,569 B2 | 9/2012 | Hestad et al. |
| D668,333 S | 10/2012 | Lee |
| 8,317,693 B2 | 11/2012 | Grey et al. |
| 8,409,088 B2 | 4/2013 | Grey et al. |
| 8,460,185 B2 | 6/2013 | Epstein et al. |
| 8,684,577 B2 | 4/2014 | Vayser |
| 8,747,394 B2 | 6/2014 | Belson et al. |
| 8,864,657 B2 | 10/2014 | Tydlaska |
| 8,876,709 B2 | 11/2014 | Vayser et al. |
| D719,652 S | 12/2014 | Swift |
| 8,899,809 B2 | 12/2014 | Vayser et al. |
| 8,992,425 B2 | 3/2015 | Karpowicz et al. |
| 9,011,323 B2 | 4/2015 | Vayser et al. |
| 9,031,628 B2 | 5/2015 | Mao et al. |
| 9,125,587 B2 | 9/2015 | Hawkins et al. |
| D740,098 S | 10/2015 | Kuo et al. |
| 9,718,130 B1 | 8/2017 | Vayser et al. |
| D805,641 S | 12/2017 | Gu |
| D809,138 S | 1/2018 | Khan et al. |
| 2005/0240081 A1 | 10/2005 | Eliachar |
| 2006/0084032 A1 | 4/2006 | Tipton et al. |
| 2006/0217596 A1 | 9/2006 | Williams |
| 2007/0060795 A1 | 3/2007 | Vayser et al. |
| 2007/0066872 A1 | 3/2007 | Morrison et al. |
| 2007/0112257 A1 | 5/2007 | Hensler |
| 2007/0270656 A1* | 11/2007 | Bayat ................. A61B 17/02 600/214 |
| 2008/0132766 A1 | 6/2008 | Dant et al. |
| 2010/0022843 A1* | 1/2010 | Pecherer ............ A61B 1/00034 600/197 |
| 2010/0069722 A1 | 3/2010 | Shalman et al. |
| 2010/0298648 A1 | 11/2010 | Gray |
| 2012/0059226 A1 | 3/2012 | Funt |
| 2012/0116170 A1 | 5/2012 | Vayser et al. |
| 2012/0245431 A1 | 9/2012 | Baudouin et al. |
| 2013/0197313 A1 | 8/2013 | Wan |
| 2014/0012090 A1 | 1/2014 | Heitland et al. |
| 2014/0221763 A1 | 8/2014 | Vayser et al. |
| 2014/0296645 A1* | 10/2014 | McGrath ............ A61B 1/00101 600/186 |
| 2014/0323811 A1 | 10/2014 | DeSantis et al. |
| 2015/0080666 A1 | 3/2015 | Vayser et al. |
| 2015/0250555 A1 | 9/2015 | Haverich et al. |
| 2016/0008088 A1 | 1/2016 | Vayser et al. |
| 2016/0030128 A1 | 2/2016 | Duggal et al. |
| 2016/0100751 A1 | 4/2016 | Davis et al. |
| 2016/0151058 A1 | 6/2016 | Ferro et al. |
| 2016/0151116 A1 | 6/2016 | Wayne et al. |
| 2016/0192921 A1 | 7/2016 | Pimenta et al. |

OTHER PUBLICATIONS

Medtronic RadiaLux Lighted Retractor, as posted at Medtronic.com [online], no posting date available, [site visited Mar. 28, 2018]. Available from the Internet, <URL:https://www.medtronic.com/us-en/healthcare-professionals/products/general-surgery/lighted-retractors/radialux.html> (6 pages).

Invuity Retractor (pictured on p. 1 & 2), as posted at Invuity.com [online], posting date not available, [site visited Mar. 29, 2018]. Available from the Internet, <URL:https://invuity.com/products/retractors/eikon-lt/> (3 pages).

Non-Final Office Action for U.S. Appl. No. 29/591,770 dated Apr. 11, 2018 (16 pages).

* cited by examiner

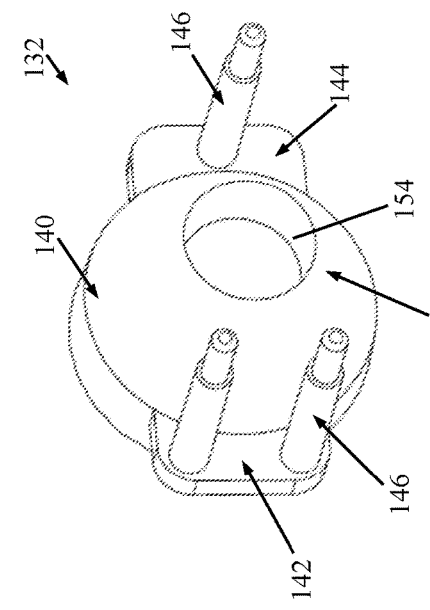
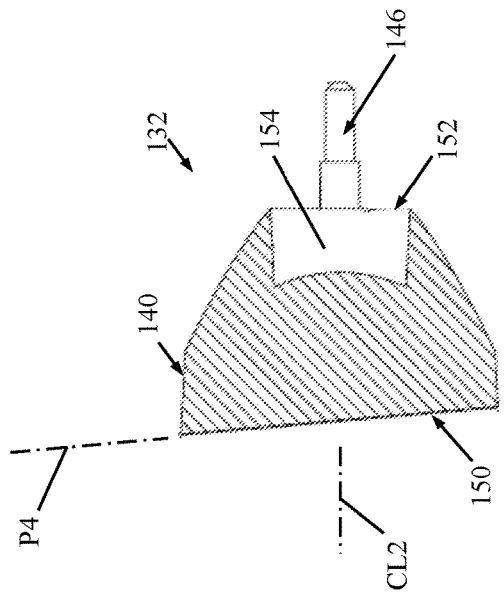
FIG. 5A
FIG. 5B
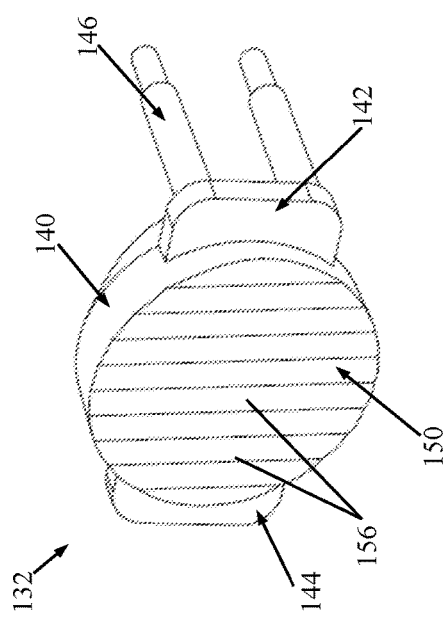
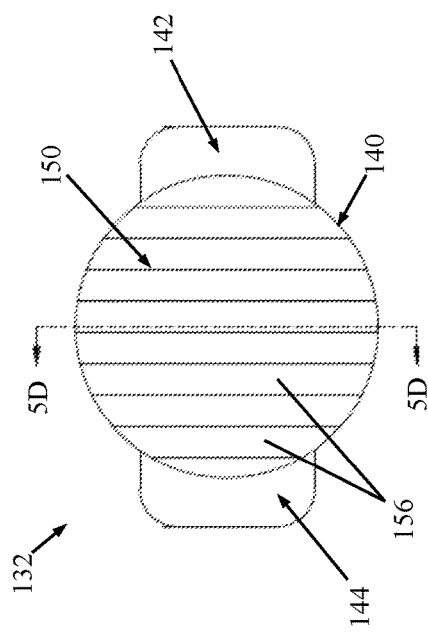
FIG. 5C
FIG. 5D

MODULAR LIGHTED SURGICAL RETRACTOR

CROSS-REFERENCE TO RELATED APPLICATIONS

This Non-Provisional patent application claims the benefit of the filing date of U.S. Provisional Patent Application Ser. No. 62/449,650, filed Jan. 24, 2017, entitled "Modular Lighted Surgical Retractor," the entire teachings of which are incorporated herein by reference.

BACKGROUND

The present disclosure relates to surgical tools. More particularly, it relates to hand held retractor instruments for use in surgical procedures, for example in retracting tissue, organs, etc.

With many surgical procedures, tissue at or leading to the intended surgical site must be retracted or moved, providing a clear and/or stabilized view of the operating field. Various hand held surgical tools (commonly referred to as a retractor) have been developed for accomplishing these purposes. Retractors generally include a handle and a blade. The blade extends from the handle at an approximately 90 degree angle, and is typically sized and shaped for a particular procedure (e.g., a longer and/or wider blade may be appropriate for retracting tissue deep inside a body of the patient, whereas a shorter and/or narrower blade may be more appropriate for retracting skin at an incision). So as to meet the needs of various surgical procedures, a surgical team normally must have a large number of differently-configured retractors available.

Although the retraction of tissue with a retractor can provide a more direct field of vision to the intended surgical site, additional illumination is oftentimes required. In some instances, the surgeon may use a separate light source such as a head-mounted light or other light source located in the surgical suite. More recently, lighted retractors have been suggested with which a fiber optic light guide is loaded to the retractor body itself. With this approach, light from the fiber optic light guide can be emitted more directly over and along a face of the blade, thus more directly illuminating the surgical site. While beneficial, fiber optic light guides are relatively expensive and may negatively affect a surgeon's ability to freely move his or her hands. Further, light may not be provided at a location desired by the user, and power requirement may be excessive.

SUMMARY

The inventors of the present disclosure recognized that a need exists for surgical retractors that overcome one or more of the above-mentioned problems.

Some aspects of the present disclosure are directed toward a modular surgical retractor including a handle and a blade. The handle includes a base and a neck. The base defines opposing, first and second ends. The neck projects from the first end of the base to a tail region. The blade includes a head section and a blade member. The head section includes a first side wall, an opposing second side wall, and a floor. The side walls and the floor combine to define a slot sized to receive the neck. The blade member projects from the head section. The handle and the blade are configured to provide an attached state in which the blade is removably attached to the handle. In the attached state, an attachment face of each of the side walls is in contact with the first end of the base, and the floor is in contact with the tail region. With this construction, the blade can be robustly attached to the handle in a manner providing an enhanced interface sufficient to maintain a structural integrity of the retractor when the blade member is subjected to expected tissue lifting or retraction forces. In some embodiments, the surgical retractor further includes a light source, such as an LED, disposed within the neck and arranged to emit light along a face of the blade member. In related embodiments, the surgical retractor further includes a lens configured and arranged to focus light from the LED at a desired location. In other related embodiments, the surgical retractor includes a power regulation circuit that provides power for an extended period of time using a small amount of power capacity (e.g., on the order of two hours of operation using two AA batteries). In other embodiments, the floor and an inside face of the neck form similarly-shaped curved regions that promote attachment of the blade to the handle via rotation. In yet other embodiments, two or more additional blades are provided, with each additional blade including the head section as described above along with a differently sized and/or shaped blade member.

BRIEF DESCRIPTION OF THE DRAWINGS

FIG. 5A is a front perspective view of a lens useful with the handle assembly of FIG. 2;

FIG. 5B is a rear perspective view of the lens of FIG. 5A;

FIG. 5C is a front plan view of the lens of FIG. 5A;

FIG. 5D is a cross-sectional view of the lens of FIG. 5C, taken along the line 5D-5D;

DETAILED DESCRIPTION

Figure 1A:
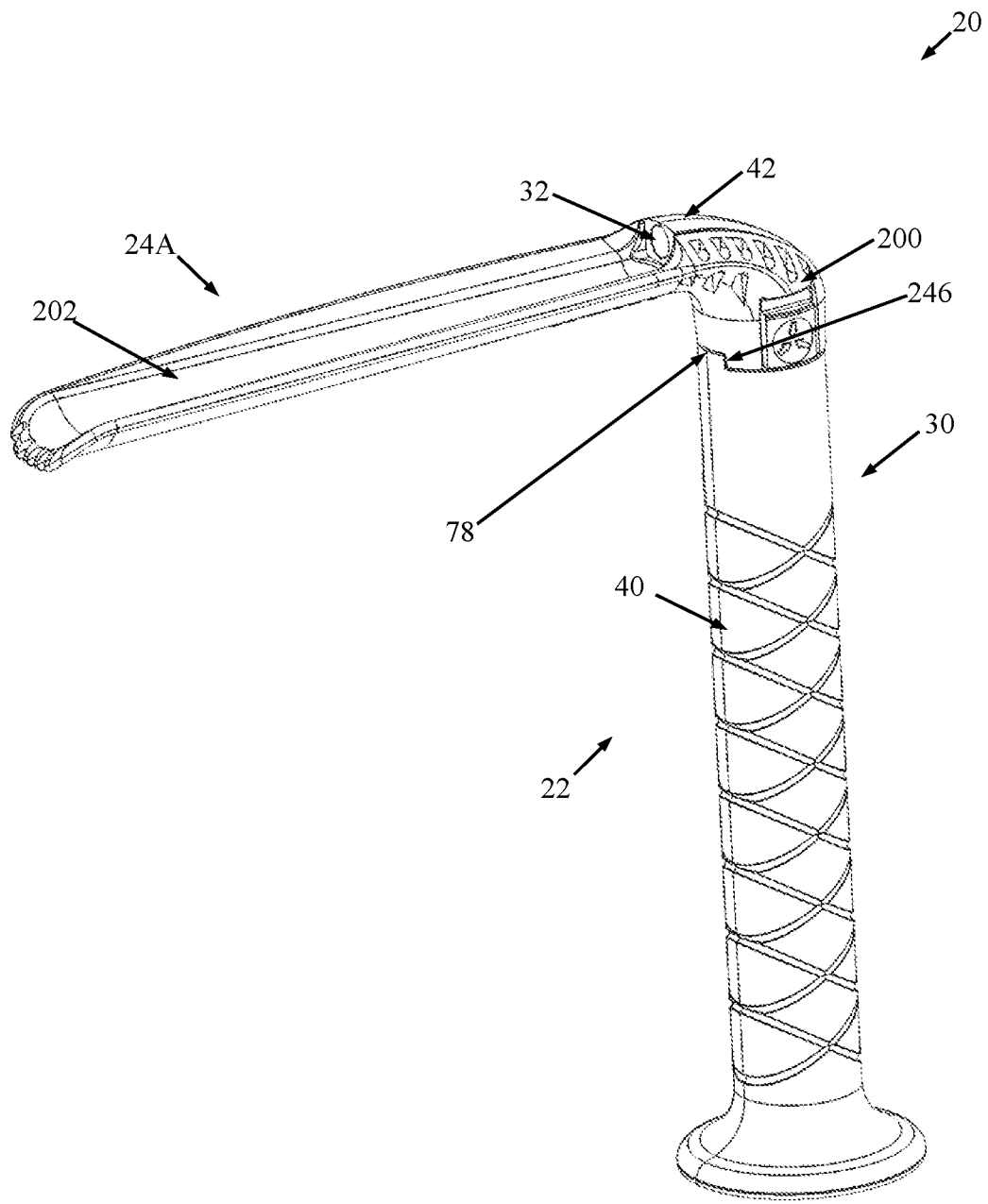
FIG. 1A is a perspective view of a modular surgical retractor in accordance with principles of the present disclosure including a blade attached to a handle assembly.
Figure 1B:
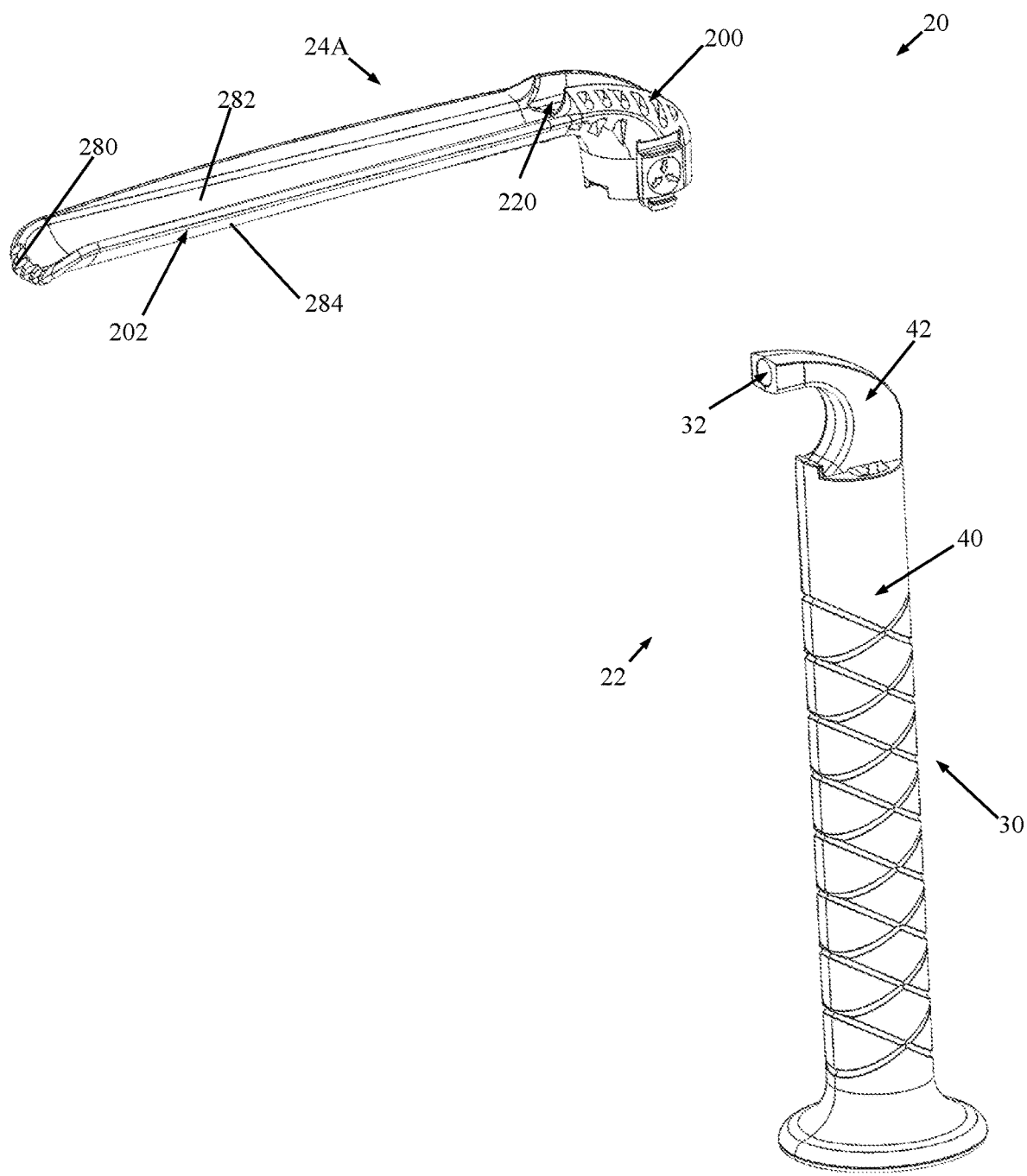
FIG. 1B is a perspective view of the modular surgical retractor of FIG. 1A and illustrating the blade removed from the handle assembly.

One embodiment of a modular surgical retractor 20 in accordance with principles of the present disclosure is shown in FIGS. 1A and 1B. The surgical retractor 20 includes a handle assembly 22 and at least one blade, such as a first blade 24A. Details on the various components are provided below. In general terms, the handle assembly 22 includes a handle 30 maintaining a light source assembly 32 (referenced generally in FIGS. 1A and 1B). The handle 30 and the blade 24A incorporate complementary mating features that facilitate selective, robust attachment of the blade 24A to the handle 30 in the attached state of FIG. 1A. The light source assembly 32 is arranged to emit light along the blade 24A in the attached state. The complementary mating features allow the blade 24A to be readily, manually removable from the handle 30 (as in FIG. 1B). Once removed, another, potentially differently-configured blade can be attached to the handle 30 as described below.

The handle 30 can assume various forms, and includes or defines a base 40 and a neck 42. The base 40 and the neck 42 can be integrally formed as a continuous, homogenous structure in some embodiments. Further, the handle 30 is configured to maintain other components of the handle assembly 22. For example, and with reference to the exploded view of the handle assembly 22 in FIG. 2, in addition to the handle 30 and the light source assembly 32, the handle assembly 22 can include a power source 50 and a power delivery assembly 52. The handle 30 can be formed by first and second handle segments 54, 56 that are separately formed and, upon final assembly, collectively form the base 40 and the neck 42 (best identified in FIGS. 1A and 1B). Other constructions are also acceptable that may or may not include two or more components separately formed and subsequently assembled to complete the handle 30. Regardless, the base 40 can form or define a cavity 60 (referenced generally) within which the power source 50 and the power delivery assembly 52 are maintained, and the neck 42 can form or define a passage 62 within which the light source assembly 32 is maintained.

Figure 3A:
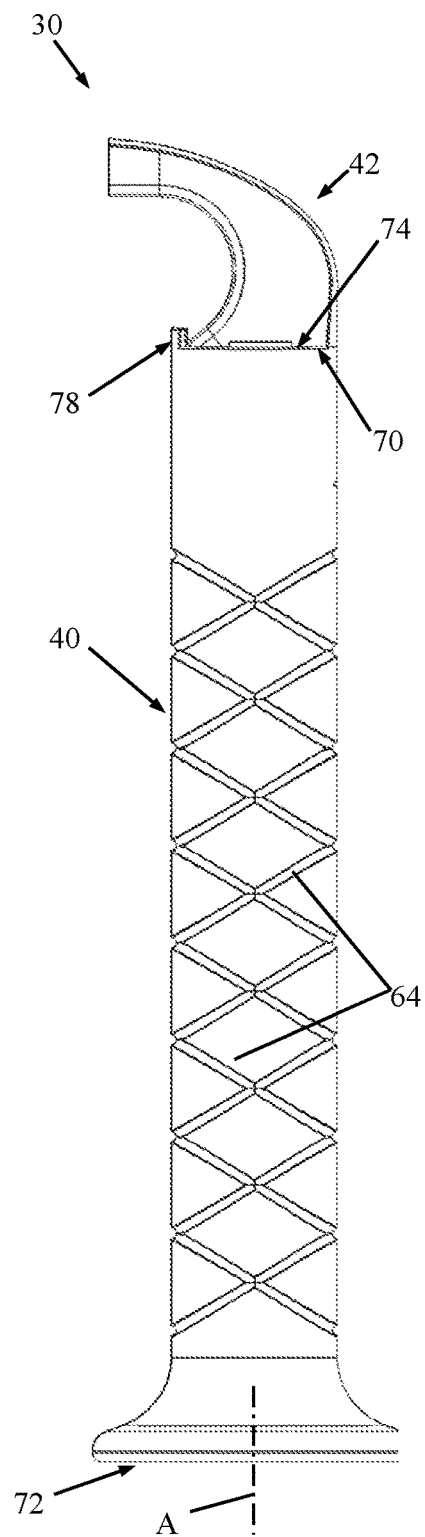
FIG. 3A is a side plan view of a handle of the handle assembly of FIG. 2.
Figure 3B:
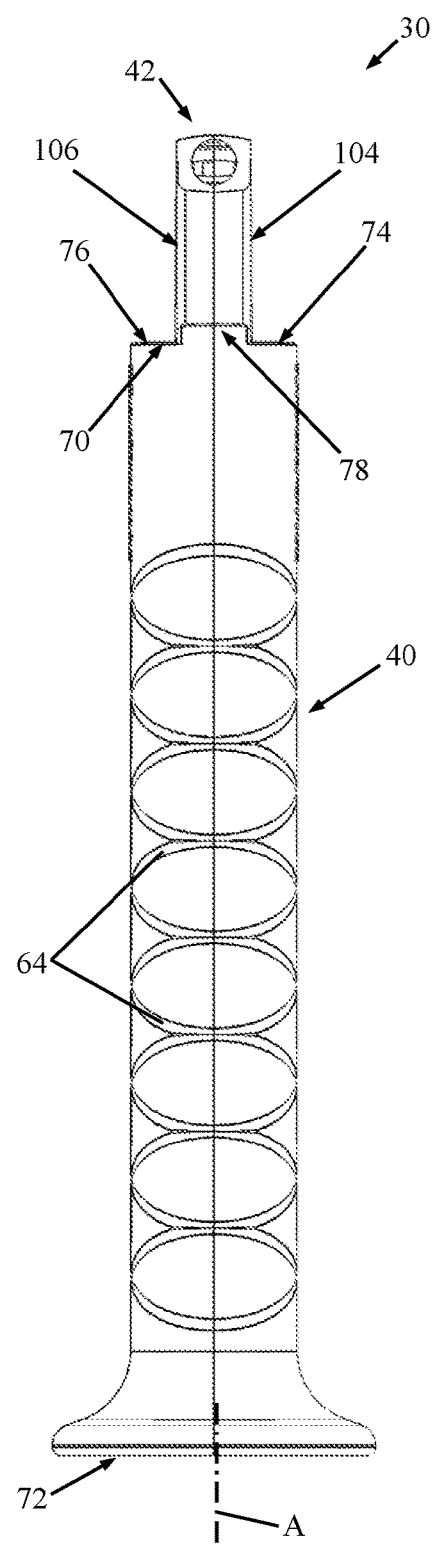
FIG. 3B is an end plan view of the handle of FIG. 3A.

With reference to FIGS. 3A and 3B, the base 40 is generally configured for grasping or handling by an adult human hand, and can have the elongated, cylindrical-like shape as shown. Other shapes are also acceptable, and an exterior of the base 40 optionally includes texturing 64 (referenced generally) that promotes gripping of the base 40 by a user's hand. For example, a coating, sleeve, skin, etc., can be applied to an exterior of the base 40 (and the neck 42) that provides the texturing 64 or other grip-enhancing feature. Regardless, the elongated shape defines a longitudinal axis A, with the base 40 extending along the longitudinal axis A and terminating at opposing, first and second ends 70, 72. The neck 42 projects from the first end 70 as described in greater detail below. The second end 72 can have a variety of forms, and in some embodiments has an expanded outer dimension (e.g., diameter) as compared to a remainder of the base 40 serving as a platform for supporting the handle 30 in an upright positioned when placed on a flat surface.

Figure 3D:
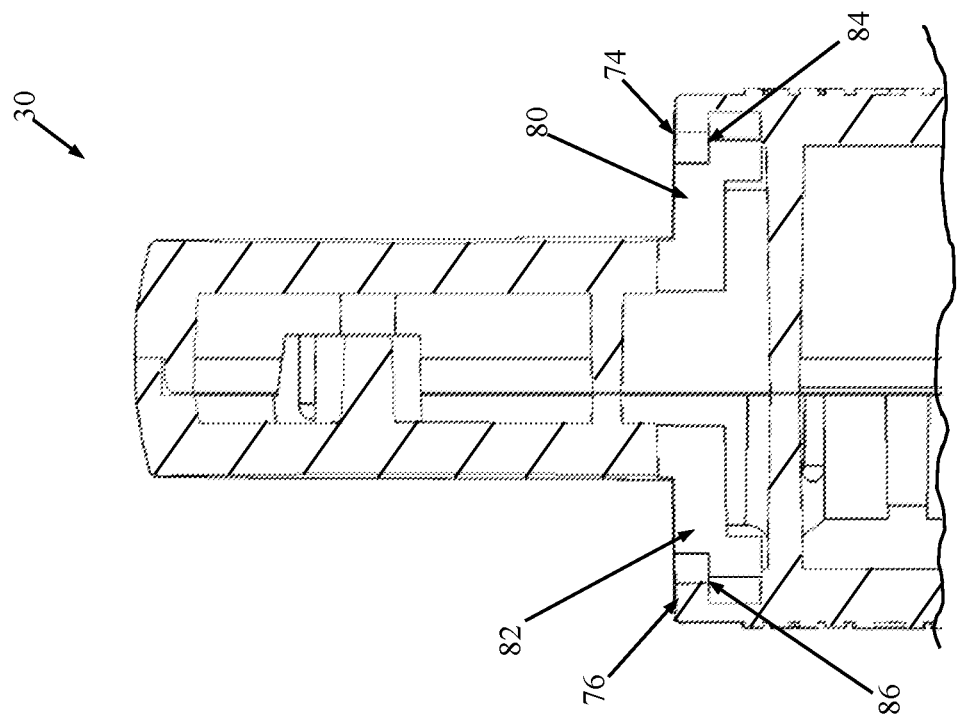
FIG. 3D is a cross-sectional view of the handle of FIG. 3C, taken along the line 3D-3D.
Figure 3C:
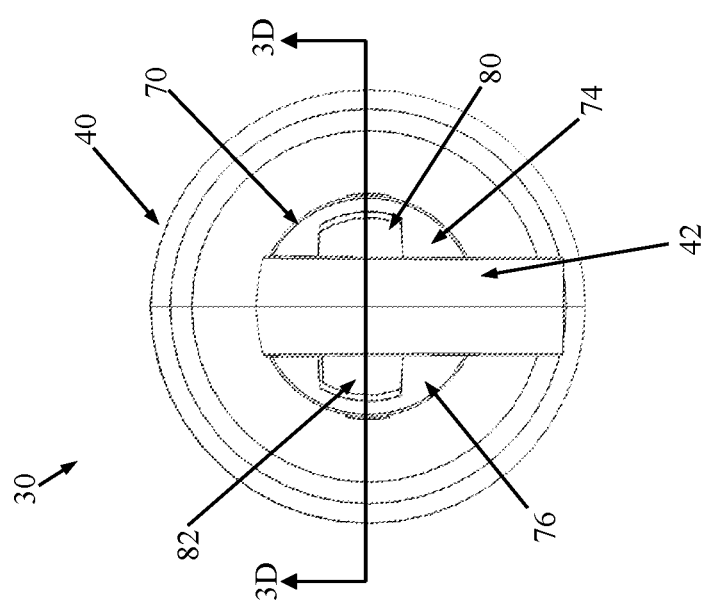
FIG. 3C is a top plan view of the handle of FIG. 3A.

With additional reference to FIG. 3C, the first end 70 can have a generally circular shape, with the neck 42 being centrally disposed within a shape of the first end 70. In some embodiments, a size and shape of the neck 42 (at least at a point of intersection with the first end 70) are less than that of the first end 70, and the neck 42 is centrally located relative to the first end 70. With this construction, one or more shoulders, such as first and second shoulder segments 74, 76, are established along the first end 70. The shoulder segments 74, 76 are located at opposite sides of the neck 42 and in some embodiments are substantially flat (i.e., within 5% of a truly flat surface). A latch 78 can be formed as an outward projection from the first end 70 and that is aligned with the neck 42. A notch 80, 82 can be defined in each of the shoulder segments 74, 76, respectively. As shown in FIG. 3D, the base 40 forms a first interior ledge 84 adjacent the notch 80 in the first shoulder segment 74, and a second interior ledge 86 adjacent the notch 82 in the second segment 76. The shoulder segments 74, 76, the latch 78, the notches 80, 82, and the interior ledges 84, 86 are configured to interface with corresponding features of the blade 24A (FIGS. 1A and 1B) as described below.

Figure 4B:
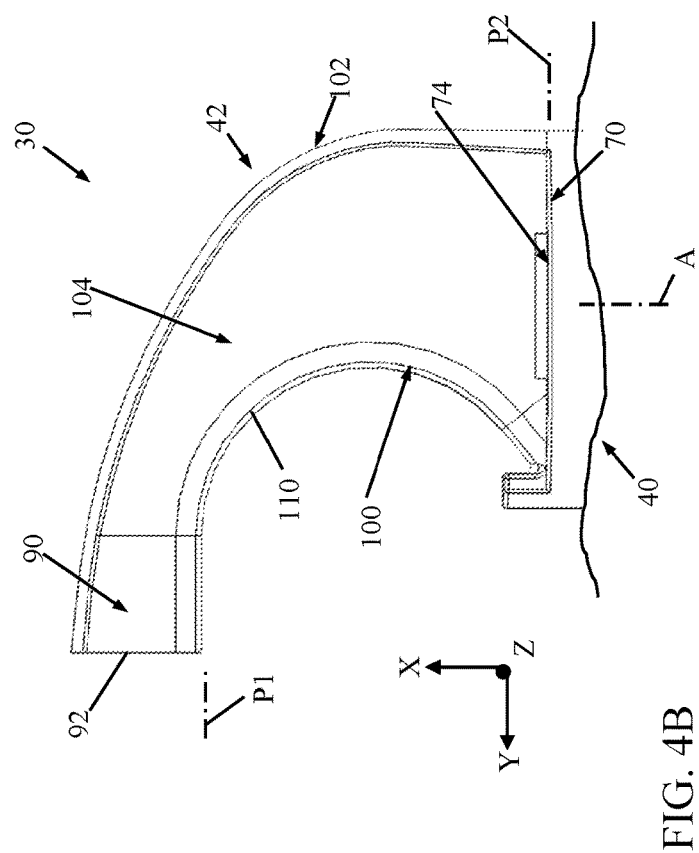
FIG. 4B is a side plan view of the neck of the handle of FIG. 4A.
Figure 4A:
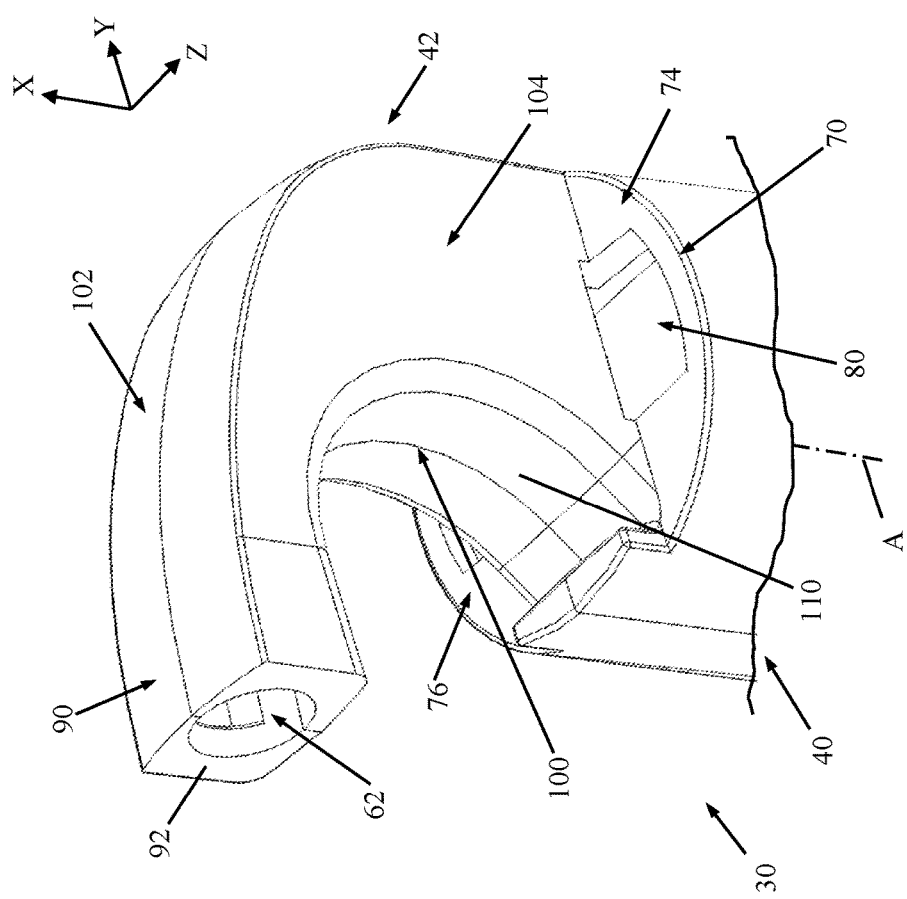
FIG. 4A is an enlarged perspective view of a neck portion of the handle of FIG. 3A.

The neck 42 is shown in greater detail in FIGS. 4A and 4B, and projects from the first end 70 of the base 40 to a tail region 90. The tail region 90 terminates at a tail end 92. As most clearly seen in FIG. 4A, the passage 62 is open to or at the tail end 92. A geometry of the neck 42 in extension from the first end 70 spatially off-sets the tail region 90, including the tail end 92, relative to the first end both longitudinally and transversely in some embodiments. In this regard, the longitudinal axis A is identified in FIGS. 4A and 4B, along with an X, Y, Z coordinate system. The longitudinal axis A corresponds with the X axis. The Y axis is orthogonal to the X axis, and the Z axis is orthogonal to the X and Y axes. With these conventions in mind, and as best reflected in FIG. 4B, projection of the neck 42 locates the tail region 90 and the tail end 92 to be off-set from the first end 70 along the X axis (longitudinal) and the Y axis (transverse) (e.g., the tail region 90 and the tail end 92 are "above" and "leftward" of the first end 70 relative to the orientation of FIG. 4B). Stated otherwise, the tail region 90 and the tail end 92 are off-set from the first end 70 in both a longitudinal direction that is otherwise parallel with the longitudinal axis A and in a transverse direction that is otherwise perpendicular to the longitudinal axis A.

The neck 42 can incorporate various shapes in establishing the above-described spatial relationship of the tail region 90 and the tail end 92 relative to the first end 70 of the base 40. In some embodiments, a shape of the neck 42 can be described as including or defining an inside face 100, an outside face 102, and opposing, first and second side faces 104, 106 (the second side face 106 is hidden in FIGS. 4A and 4B, and is generally identified in FIG. 3B). In some embodiments, at least a portion, for example a guide portion 110, of the inside face 100 is curved in extension from the base 40. A curvature established by the inside face 100 can be or include a concave curve relative to the longitudinal axis A. In some embodiments, a relatively uniform curvature or radius of curvature can be established along at least a majority of the guide portion 110. In other embodiments, the inside face 100 can have a complex or non-uniform curvature, can be curvilinear, or can be linear in extension from the base 40 to the tail region 90. Regardless, in some embodiments and as best reflected by FIG. 4B, the inside face 100 is substantially flat (i.e., within 5% of a truly flat surface) along the tail region 90. In related optional embodiments, a major plane P1 established by the inside face 100 along the tail region 90 is substantially parallel (i.e., within 5 degrees of a truly parallel relationship) with a major plane P2 of the shoulder segments 74, 76 for reasons made clear below.

Figure 2:
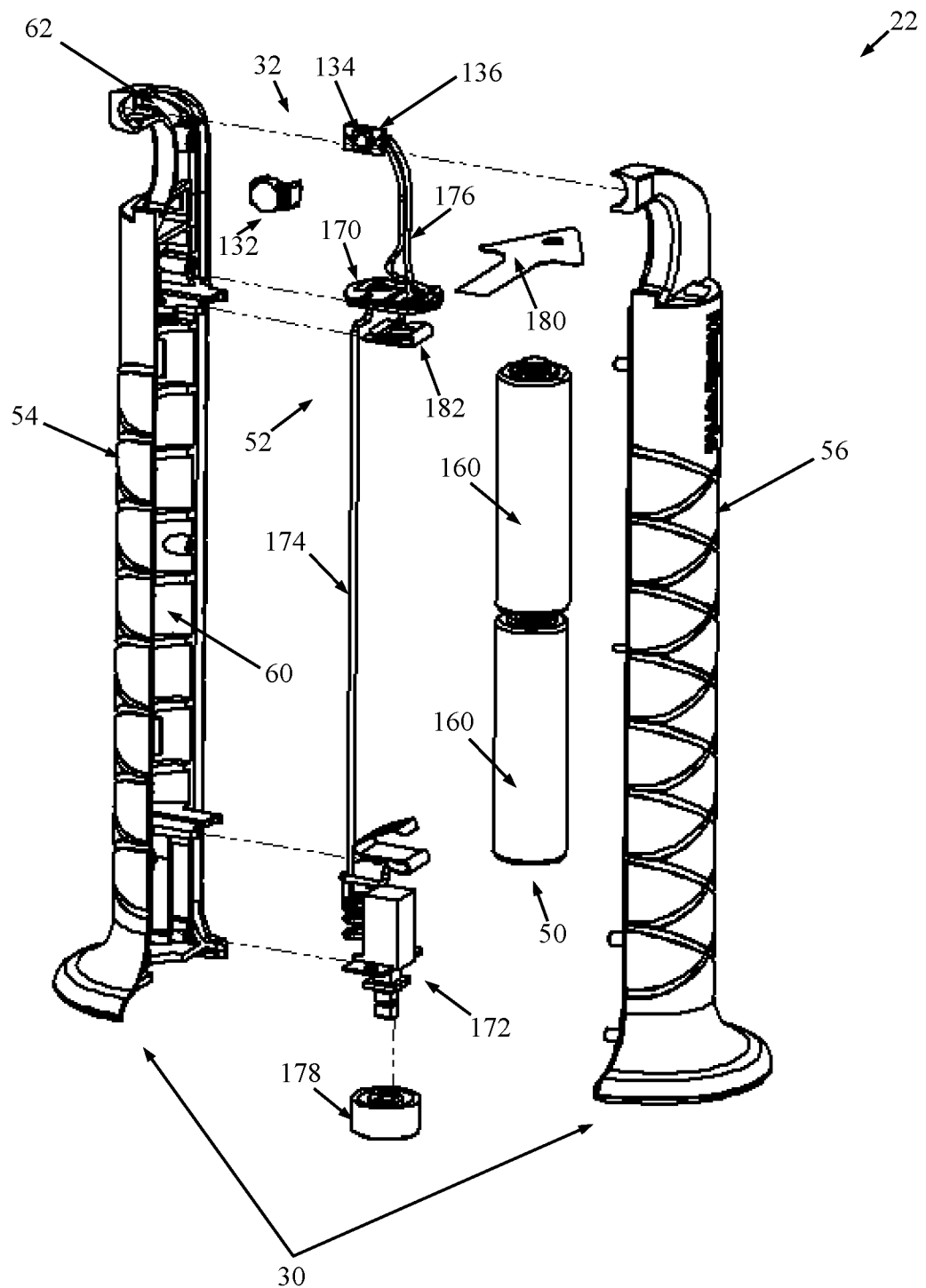
FIG. 2 is an exploded perspective of the handle assembly of FIG. 1A.

The outside face 102 optionally has a curvature generally mimicking that of the inner face 100 to establish a streamlined shape, with the neck 42 generally tapering in the transverse direction (Y axis) in extension from the base 40. In some embodiments, the outside face 102 can project away from the inside face 100 along the tail region 90 in extension to the tail end 92; with this optional geometry, the passage 62 can be appropriately sized to receive the light source assembly 32 (FIG. 2).

The side faces 104, 106 can be substantially identical in some embodiments, and are optionally substantially planar or flat. As best shown in FIG. 4A, the notch 80 in the first shoulder segment 74 can extend into or be partially formed by the first side face 104. Though hidden in the views, the notch 82 in the second shoulder segment 76 can similarly extend into or be partially formed by the second side face 106.

Figure 4C:
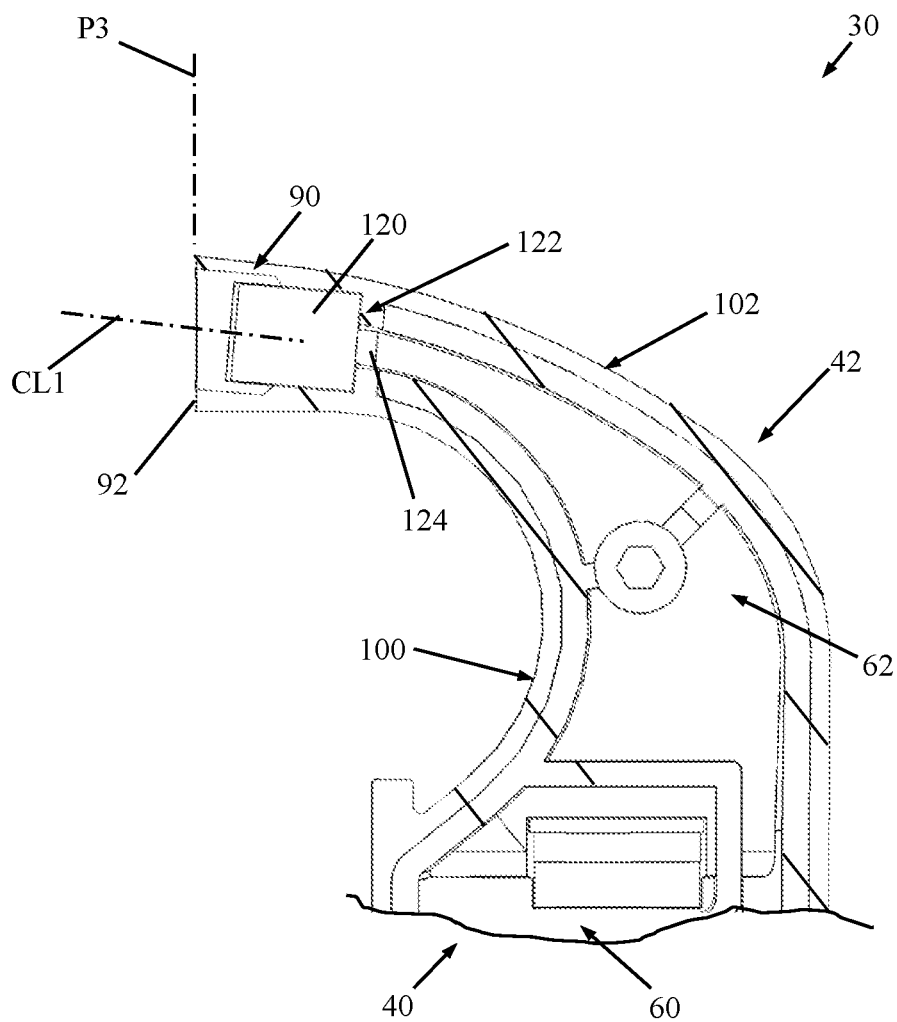
FIG. 4C is a longitudinal cross-sectional view of the neck of the handle of FIG. 4A.

The passage 62 within the neck 42 is more clearly shown in FIG. 4C. The passage 62 is open to the tail end 92 and includes or provides a pocket region 120 sized and shaped for mounting of the light source assembly 32 (FIG. 2). For example, a flange 122 can be formed at a side of the pocket region 120 opposite the tail end 92. A distance between the flange 122 and the tail end 92 corresponds with a geometry of the light source assembly 32 such that the flange 122 provides a surface against which the light source assembly 32 can be mounted at a known location relative to the tail end 92. A channel 124 is defined through the flange 122 such that the passage 62 can be continuously open to the cavity 60 in the base 40. With this optional construction, wiring (not shown) or other electrical circuitry can be routed from the base 40 to the pocket region 120 (and thus to the light source assembly 32 mounted within the pocket region 120). In some embodiments, a curvature of the inside and outside faces 100, 102 in extension from the base 40 to the tail region 90, along with the optional non-parallel relationship of the inside and outside faces 100, 102 along the tail region 90, results in a centerline CL1 of the passage 62 along the pocket region 120 being non-perpendicular (and non-parallel) to a major plane P3 of the tail end 92. As described in greater detail below, the light source assembly 32 can be configured to accommodate this off-set arrangement while maintaining the streamlined shape of the neck 42.

Returning to FIG. 2, the light source assembly 32 includes a light source 130 and an optional lens 132. The light source 130 can assume various forms, and in some embodiments includes one (or more) light emitting diodes (LEDs) 134 and corresponding circuitry (e.g., the LED 134 is attached to a circuit board 136).

The lens 132 is configured for assembly to the light source 130 and to direct or affect emitted light. One embodiment of the lens 132 is shown in greater detail in FIGS. 5A-5D. The lens 132 can include or lens body 140, opposing tabs 142, 144, and one or more fingers 146 projecting from a respective one of the tabs 142, 144. The lens body 140 can be a solid structure, formed of a material appropriate for allowing passage of light (e.g., a transparent, semi-transparent, or translucent material). The lens body 140 defines opposing, leading and trailing sides 150, 152. An aperture 154 is defined in the lens body 140 at the trailing side 152, sized and shaped to receive the LED 134 (FIG. 2). In some embodiments, the leading side 150 provides a structured or ridged surface 156 configured to focus and shape light. In other embodiments, the leading side 150 is substantially flat and does not include ridges or other light affecting structures. In some embodiments, the lens body 140 is shaped such that a major plane P4 established by the leading side 150 is non-perpendicular (and non-parallel) with a centerline CL2 of the lens body 140. This optional off-set relationship corresponds with a geometry of the neck 42 (FIG. 4C) as described above.

The tabs 142, 144 project from opposite sides of the lens body 140, and are sized and shaped for mounting within and to the neck passage 62 (FIG. 4C). The fingers 146 project from the tabs 142, 144 in a direction of and beyond the trailing side 152 of the lens body 140, and also serve to provide robust mounting within the neck passage 62. Alternatively, the lens 132 can incorporate other mounting features that may or may not include one or more of the tabs 142, 144 and/or the fingers 146.

Returning to FIG. 2, the power source 50 can assume various forms, and in some embodiments includes one or more batteries 160. The batteries 160 are selected in accordance with power requirements of the light source 130, and in some embodiments, the power source 50 consists of two, AA batteries 150 (e.g., 1.5 volt). Other power source formats are also acceptable. In yet other embodiments, the surgical retractors of the present disclosure need not incorporate a light source carried by the handle 30, and thus need not include the power source 50.

The power delivery assembly 52 is formatted for delivering power from the power source 50 to the light source 130 in an appropriate manner. In some embodiments, the power delivery assembly 52 includes a driver 170 and an actuator or switch 172. The driver 170 is electrically connected (e.g., via wiring 174) to the switch 172 that in turn is electrically connected to the power source 50. The driver 170 is further electrically connected to the light source 130 via wiring 176. As is known to those of ordinary skill, the actuator 172 can be a mechanical switch (e.g., spring-loaded) that when actuated, allows delivery of power from the power source 50 to the driver 170; subsequent actuation of the actuator 172 discontinues the delivery of power to the driver 170. A cap 178 is optionally assembled to the actuator 172 to promote user interface with the actuator 172.

Figure 6:
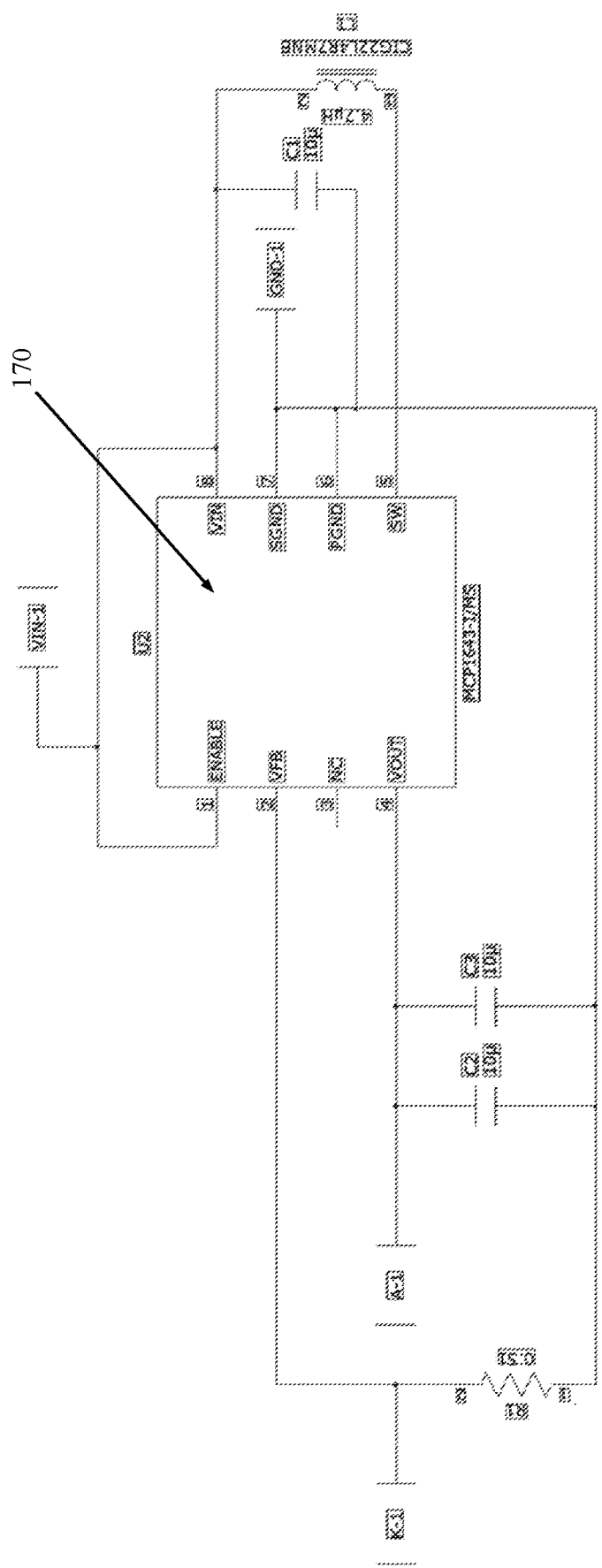
FIG. 6 is a circuit diagram of power delivery circuitry useful with the handle assembly of FIG. 2.

In some embodiments, the driver 170 is a constant current LED driver of a type known in the art. By way of one non-limiting example, the driver 170 can be a constant current LED driver available from Microchip Technology Inc. under the trade designation MCP1643. The corresponding circuit (e.g., wiring and other electrical components) can assume various forms appropriate for supplying power to the light source 130. One non-limiting example of a circuit used to drive an LED as the light source 130 is provided in FIG. 6. As a point of reference, the circuit diagram of FIG. 6 reflects that the driver 170 is connected to a positive side of the battery through a pushbutton switch (labeled as "VIN-1"), and directly to a negative side of the power source (labeled as "GND-1"). Further, the driver 170 is directly connected to the LED cathode at "K-1" and the LED anode at "A-1". Other circuit designs are also acceptable.

Returning to FIG. 2, the power delivery assembly 52 can optionally further include a circuit interrupter strip 180. Where provided, the interrupter strip 180 is slidably disposed between a terminal of the power source 50 and the power delivery circuitry.

Prior to powering of the light source 130, the interrupter strip 180 is removed by the user, thereby completing the power delivery circuit. In other embodiments, the interrupter strip 180 can be omitted.

Figure 7A:
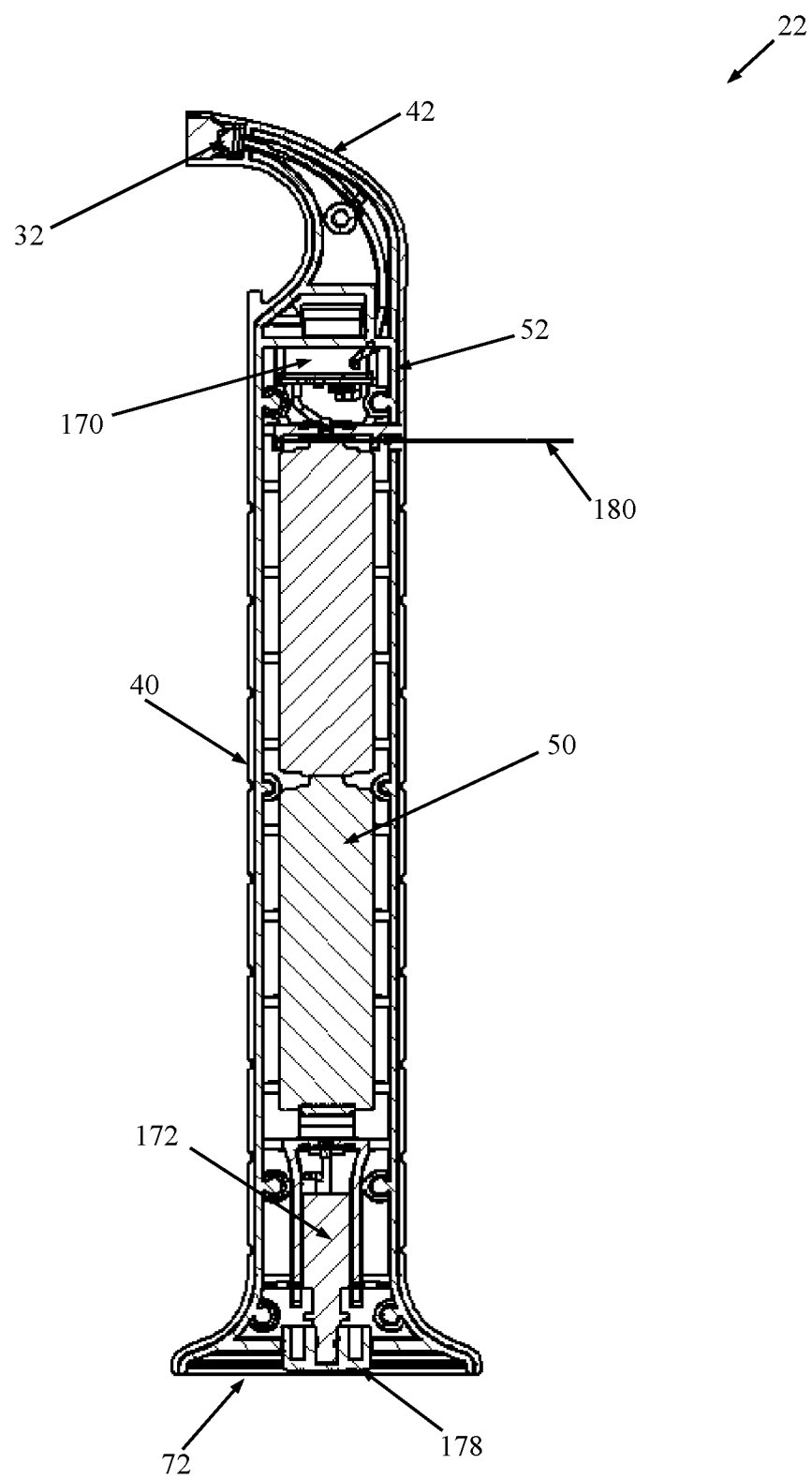
FIG. 7A is a longitudinal cross-sectional view of the handle assembly of FIG. 2 upon final assembly.

Final construction of the handle assembly 22 is shown in FIG. 7A. The power source 50 is carried by and retained within the base 40. The driver 170, along with other components of the power delivery assembly 52 (referenced generally) such as wiring (not shown) are also carried by and retained within the base 40. In this regard, the cap 178, and thus the actuator 172, is accessible at an opening in the second end 72. The interrupter strip 180, where provided, is located between a terminal of the power source 50 and a contact 182 (best seen in FIG. 2) of the power delivery assembly 52, and extends outwardly through a slot in the base 40. The interrupter strip 180 is thus accessible by a user; by pulling the interrupter strip 180 from the base 40, the power delivery circuit is complete, providing power from the power source 50 to the actuator 172, and thus the driver 170.

Figure 7B:
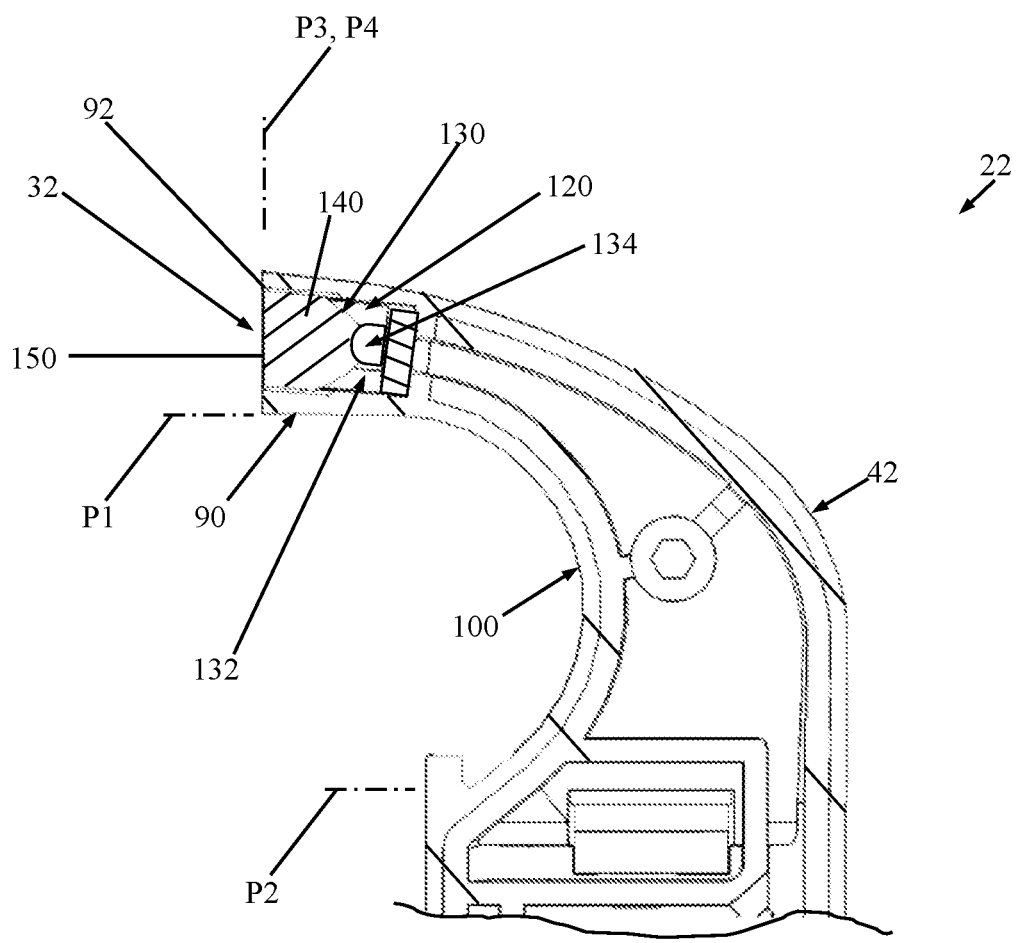
FIG. 7B is an enlarged cross-sectional view of a neck portion of the handle assembly of FIG. 7A.

Mounting of the light source assembly 32 within the neck 42 is shown in greater detail in FIG. 7B. The light source 132 is assembled to the lens 130, including the LED 134 located within the lens body 140. With additional reference to FIG. 4C, the lens 130 and the light source 132 are mounted within the pocket region 120 in a fixed manner. For example, the light source assembly 52 can be press-fit into the pocket region 120 and/or one more attachment materials (e.g., adhesive) can be employed. Regardless, in some embodiments, at least the light source 132, and optionally the lens 130, is permanently attached to the handle 30 and is not removable therefrom by a user under normal conditions of use. The leading side 150 of the lens body 140 is aligned with, optionally flush to, the tail end 92. In some embodiments, the lens body 140 is arranged such that the major plane P4 of the leading side 150 is substantially parallel with (i.e., within 5 degrees of a truly parallel relationship) the major plane P3 of the tail end 92; in related embodiments, the major planes P3, P4 are substantially co-planar (i.e., within 5 degrees of a truly co-planar relationship). With this optional construction, the substantially co-planar major planes P3, P4 can be substantially perpendicular (i.e., within 5 degrees of a truly perpendicular relationship) to one or both of the major plane P1 of the inside face 100 along the tail region 90 and the major plane P2 of the shoulder segments 74, 76 (it being understood that the shoulder segments 74, 76 are not readily evident in the cross-sectional view of FIG. 7B but are shown, for example, in FIGS. 4A and 4B).

Returning to FIGS. 1A and 1B, the first blade 24A includes or defines a head section 200 and a blade member 202. In general terms, the head section 200 is configured for removable attachment to the handle 30. The blade member 202 extends from the head section 200 and can assume various forms appropriate for certain surgical retraction procedures.

Figure 8A:
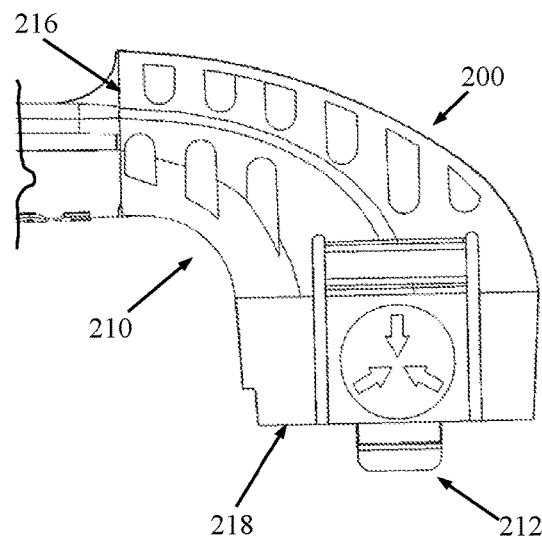
FIG. 8A is an enlarged side plan view of a portion of the blade of FIG. 1B.
Figure 8B:
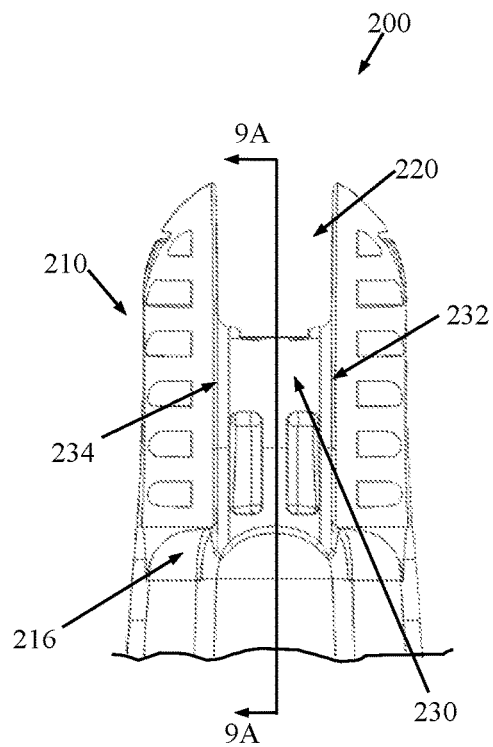
FIG. 8B is an enlarged top plan view of the portion of the blade of FIG. 8A.
Figure 8C:
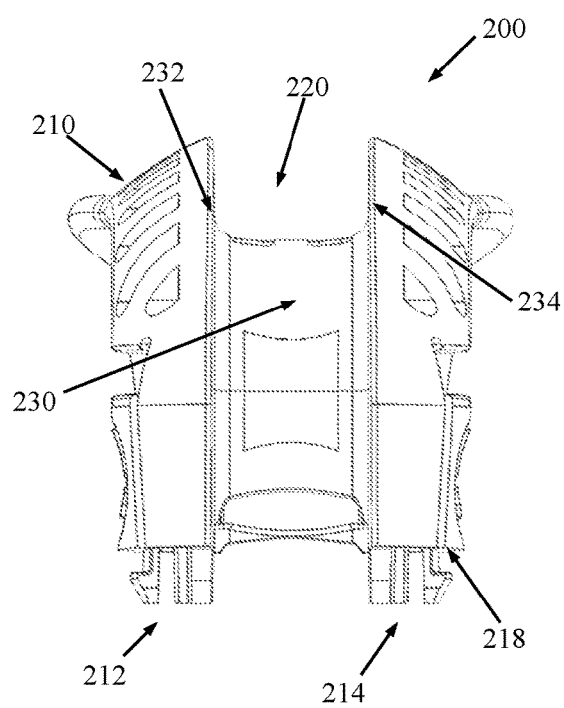
FIG. 8C is an enlarged end plan view of the portion of the blade of FIG. 8A.
Figure 9A:
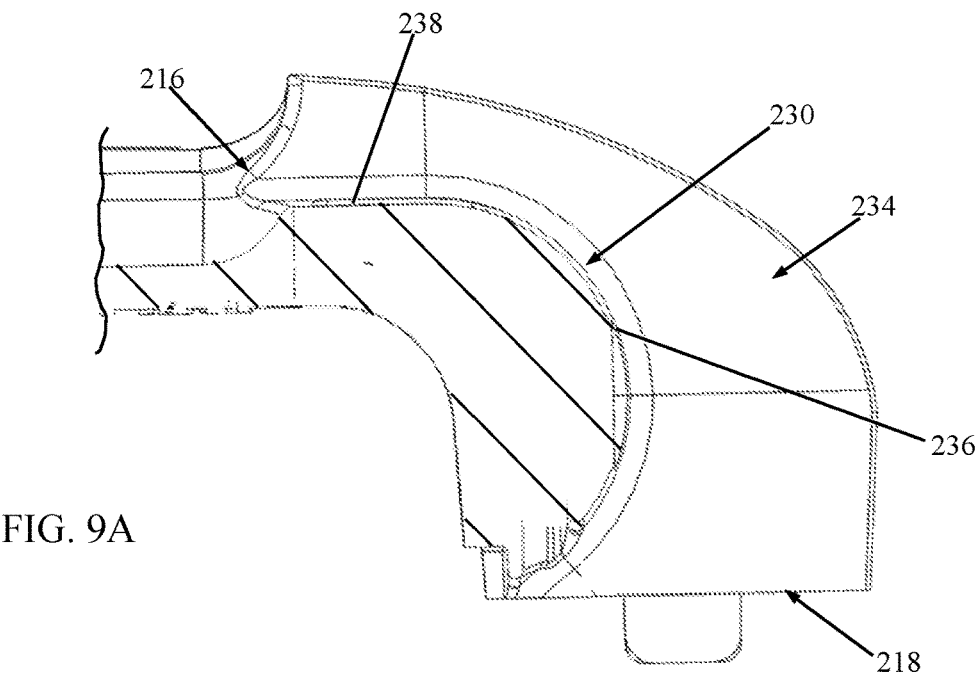
FIG. 9A is an enlarged cross-sectional view of the portion of the blade of FIG. 8B, taken along the line 9A-9A.

The head section 200 is shown in greater detail in FIGS. 8A-8C, and generally includes or defines a head body 210 and one or more clip assemblies, such as first and second clip assemblies 212, 214. The head body 210 can be an integral or homogenous structure extending between or defining a first or blade face 216 and a second or attachment face 218. The head body 210 further defines a slot 220 extending between and open to the blade and attachment faces 216, 218. As best reflected by the top view of FIG. 8B and the end view of FIG. 8C, the slot 220 can be viewed as being defined bounded by a floor 230, a first side wall 232 and an opposing, second side wall 234. As best shown in FIG. 9A, the floor 230 defines a shape or curvature that corresponds with the shape and curvature of the inside face 100 (FIG. 4B) of the neck 42 (FIG. 4B) as described above. Thus, the floor 230 can include or define a convex curved segment 236 that has substantially identical (i.e., within 5% of a truly identical relationship) geometry as the guide portion 110 (FIG. 4B). Further, the floor 230 includes or defines a contact segment 238 at or adjacent the blade face 216 that is substantially flat (i.e., within 5% of a truly flat surface) for reasons made clear below.

With continued reference to FIGS. 8A-9A, the side walls 232, 234 can be viewed as continuously extending between the blade and attachment faces 216, 218, each define an exterior shape or geometry mimicking that of the outside face 102 (FIG. 4B) of the neck 42 (FIG. 4B) as described above. Other constructions or shapes are also envisioned, and the side walls 232, 234 need not be identical.

Figure 9B:
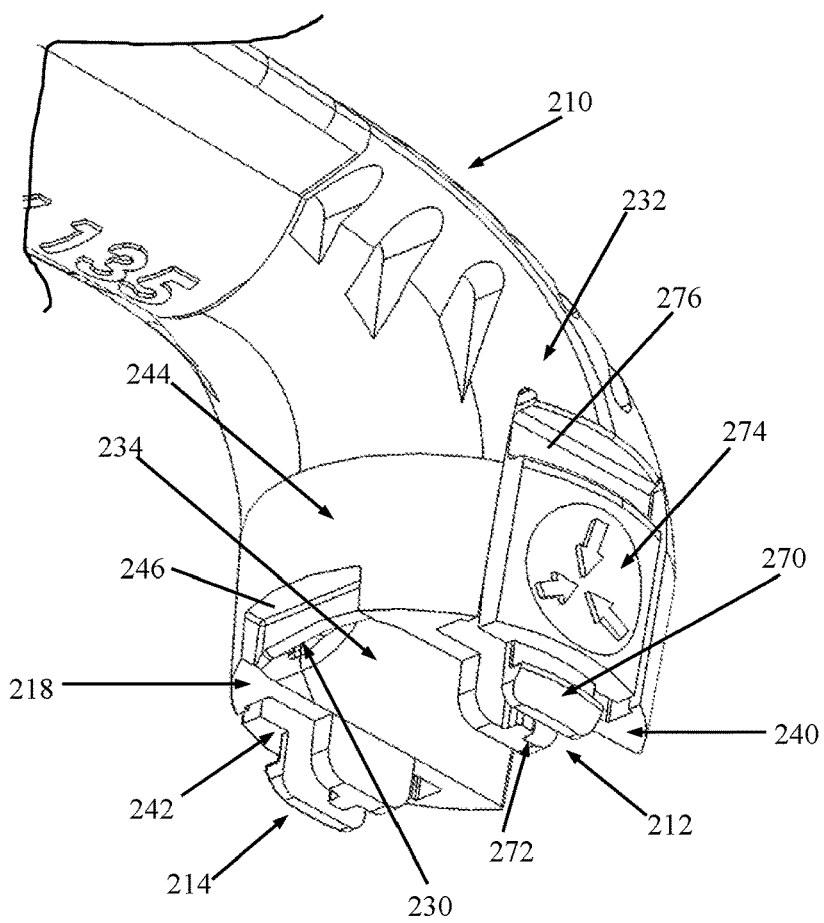
FIG. 9B is an enlarged bottom perspective view of the portion of the blade of FIG. 8A.

The attachment face 218 can be substantially flat or planar (i.e., within 5 degrees of a truly flat surface) in some embodiments as generally reflected by the figures. The perspective view of FIG. 9B illustrates that the attachment face 218 can be viewed as being formed or defined by first and second face segments 240, 242. The first face segment 240 corresponds with the first side wall 232 and the second face segment 242 corresponds with the second side wall 234. As a point of reference, the floor 230 is partially visible in the view of FIG. 9B. The face segments 240, 242 collectively define the attachment face 218 and are substantially flat and co-planar. FIG. 9B further reflects that the head body 210 can further include or define a collar 244 collectively defined by or interconnecting the floor 230 and the side walls 232, 234 apart from the attachment face 218. In some embodiments, a recess 246 can be defined through a partial thickness of the collar 244 for reasons made clear below.

The first clip assembly 212 is generally associated or aligned with the first side wall 232, and the second clip assembly 214 is generally associated with the second side wall 234. The clip assemblies 212, 214 can be identical in some embodiments, such that the following description of the first clip assembly 212 applies equally to the second clip assembly 214. The first clip assembly 212 includes a clip 270 and an optional guide member 272. The clip 270 and the guide member 272 each project from the attachment face 218 (e.g., the first face segment 240) in a laterally spaced apart arrangement. The clip 270 can be provided as part of or connected to a tab 274. The tab 274 is pivotably connected to a remainder of the head body 210 (e.g., relative to a remainder of the first side wall 232), for example at a living hinge 276, and is biased to the spatial arrangement shown. With this construction, the clip 270 can be articulated inwardly (i.e., in a direction toward the guide member 272) in response to an inward or pressing force applied to the tab 274, when the clip 270 is subjected to an inward force, etc. Upon removal of the force, the tab 274 self-reverts back to the arrangement of FIG. 9B, locating the clip 270 relative to the guide member 272 as shown. The guide member 272, where provided is more rigidly secured to the first side wall 232. As described below, the clip assemblies 212, 214 are configured to effectuate releasable engagement with the handle 30 (FIG. 2). Other attachment formats are also acceptable that may or may not include one or both of the clip assemblies 212, 214.

Figure 10:
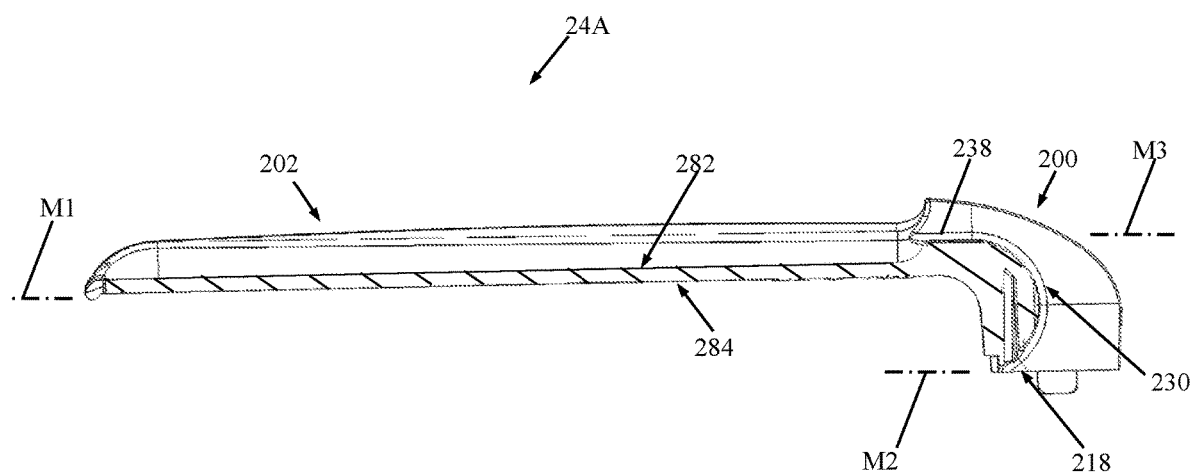
FIG. 10 is a longitudinal cross-sectional view of the blade of FIG. 1B.

Returning to FIG. 1B, the blade member 202 extends from the head section 202 to a leading edge 280. The blade member 202 can have a various shapes and sizes. In some embodiments, a shape of the blade member 202 can be viewed as defining opposing, interior and exterior surfaces 282, 284. The surfaces 282, 284 can have the uniform, curved shape as shown, or a number of other shapes that can be regular or irregular between the head section 202 and the leading edge 280. As further shown in FIG. 10, relative to a cross-sectional plane passing through a centerline of the blade member 202, the interior surface 282 is longitudinally off-set from the contact segment 238 of the floor 230 (e.g., the interior surface 282 is "below" the contact segment 238 relative to the orientation of FIG. 10). Geometry of the interior surface 282 relative to the contact segment 238 corresponds with geometry of the handle assembly 22 (FIG. 2) so as to promote desired light dispersement as described below. Further, a major plane M1 established by the exterior surface 284 (again, relative to the cross-sectional view of FIG. 10) can be substantially parallel (i.e., within 5 degrees of a truly parallel relationship) with one or both of a major plane M2 established by the attachment face 218 and a major plane M3 established by the contact segment 238 is some embodiments.

Figure 11A:
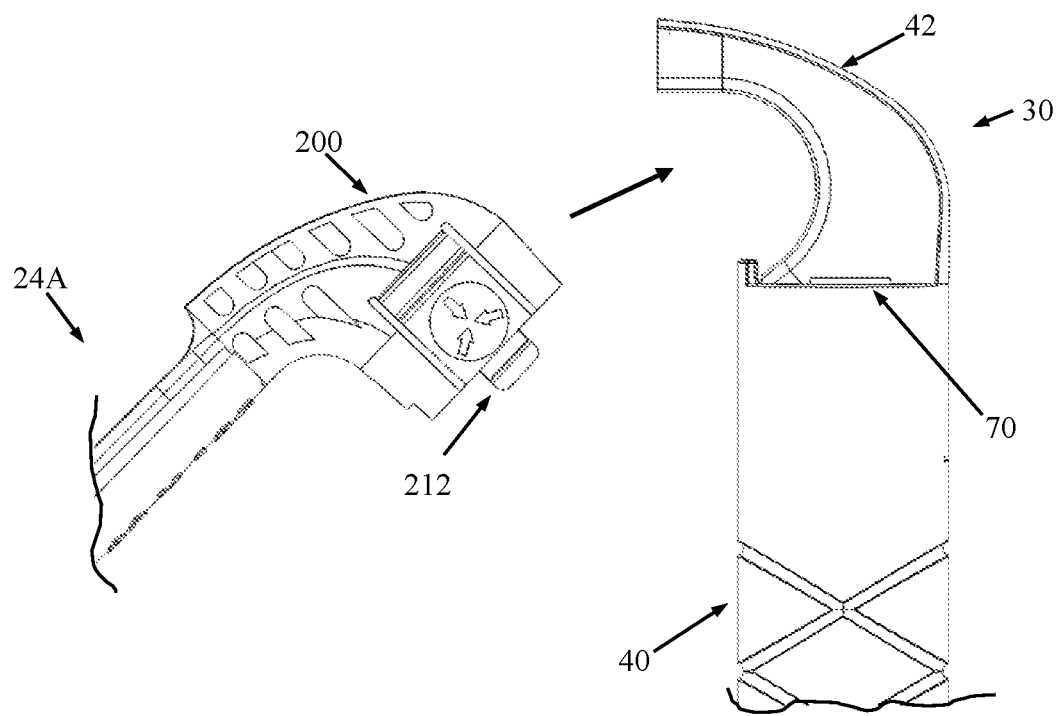
FIG. 11A is a side view of a portion of the modular surgical retractor of FIG. 1A in an initial stage of attachment of the blade to the handle assembly.
Figure 11B:
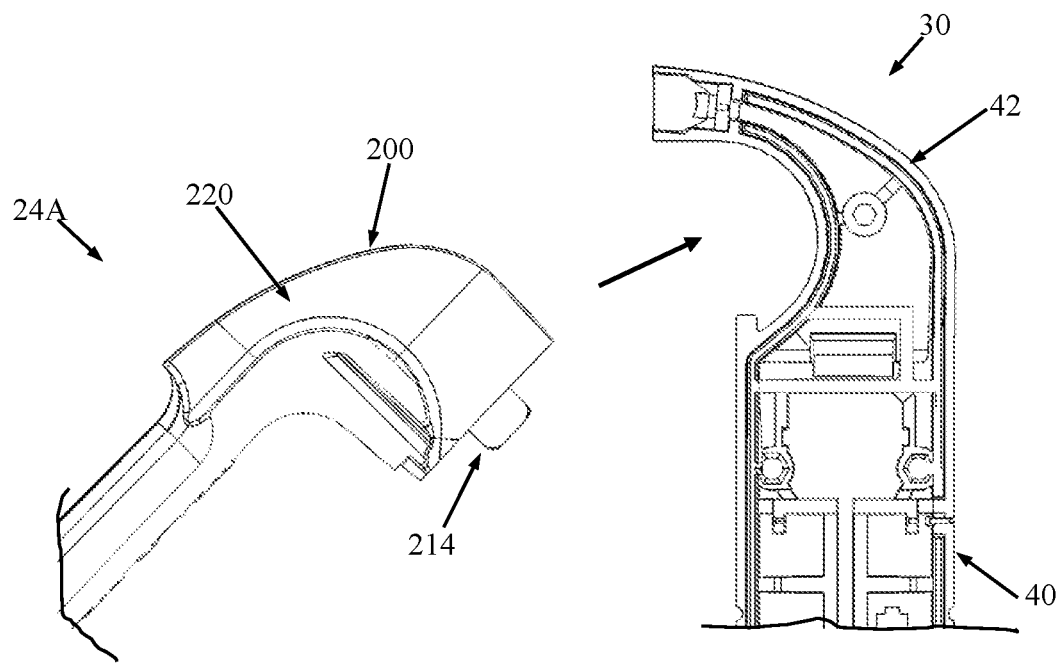
FIG. 11B is a longitudinal cross-sectional view of the arrangement of FIG. 11A.

The blade 24A can be manually attached to the handle 30 in a simple and straightforward manner. A shown in FIGS. 11A and 11B, the blade 24A is initially spatially arranged relative to the handle assembly 22 such that the slot 220 (referenced generally in FIG. 11B, more clearly shown, for example, in FIG. 1B) is generally aligned with neck 42. Further, the blade 24A is generally spatially rotated relative to the handle 30 as shown such that clip assemblies 212, 214 "clear" the first end 70 of the base 40 as the head section 200 is subsequently directed toward the neck 42 in a direction indicated by an arrow in FIGS. 11A and 11B.

Figure 12A:
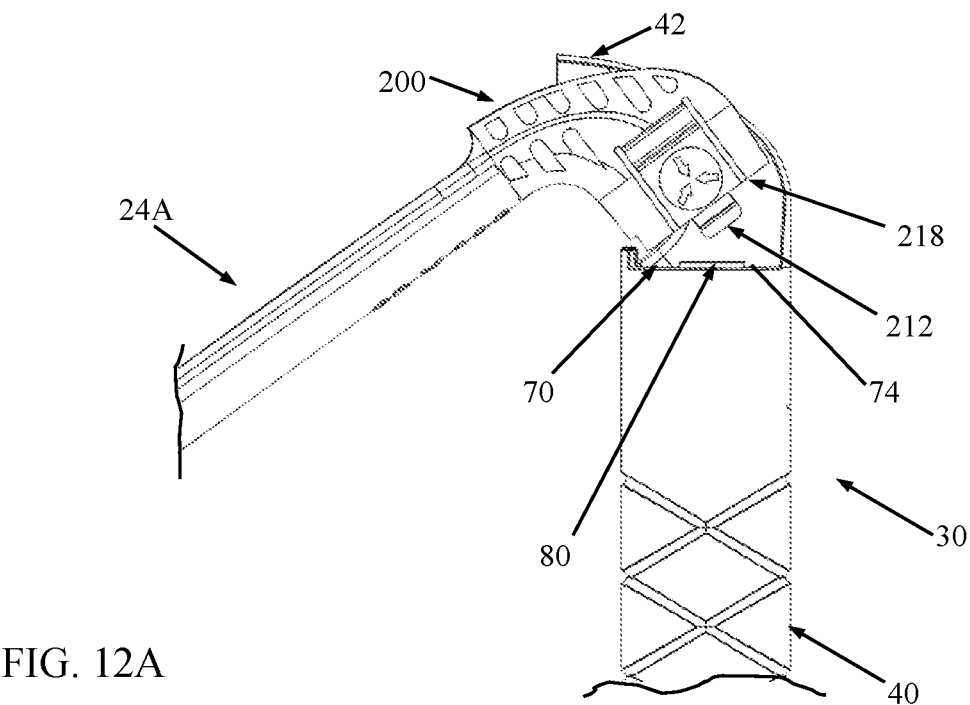
FIG. 12A is a side view of a portion of the modular surgical retractor of FIG. 1A in an intermediate stage of attachment of the blade to the handle assembly.
Figure 12B:
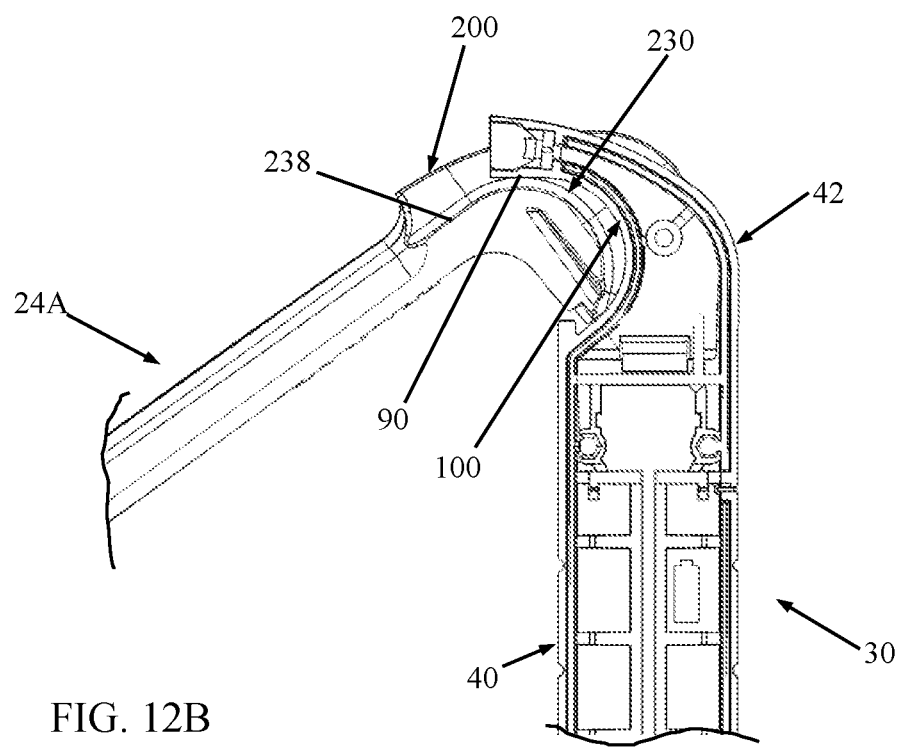
FIG. 12B is a longitudinal cross-sectional view of the arrangement of FIG. 12A.

Directing of the head section 200 onto the neck 42 is shown in FIGS. 12A and 12B. The neck 42 is generally located within the slot 220, with the floor 230 contacting the inside face 100 (best seen in FIG. 12B). In this intermediate stage of attachment, the clip assemblies 212, 214 (one of which is visible in FIG. 12A) are spaced from the first end 70 of the base 40, and are away from the corresponding notch 80, 82 (one of which is partially visible in FIG. 12A).

The blade 24A is then rotated relative to the handle 30 (and/or vice-versa), sliding and pivoting along the contacting interface between the floor 230 and the inside face 100 of the neck 42. The matching geometry of the floor 230 and the inside face 100 promotes the clip assemblies 212, 214 becoming aligned with the corresponding notch 80, 82. Further, the attachment surface 218 of the blade 24A is brought into contact with the shoulder segments 74, 76 (one of which is visible in FIG. 12A) of the handle 30. Contact between the attachment surface 218 and the shoulder segments 74, 76 serves as a stop to further rotation. Optionally, a stop to further rotation is also provided by contact between substantially flat contact segment 238 of the floor 230 and the substantially flat inside face 100 along the tail region 90.

Figure 13A:
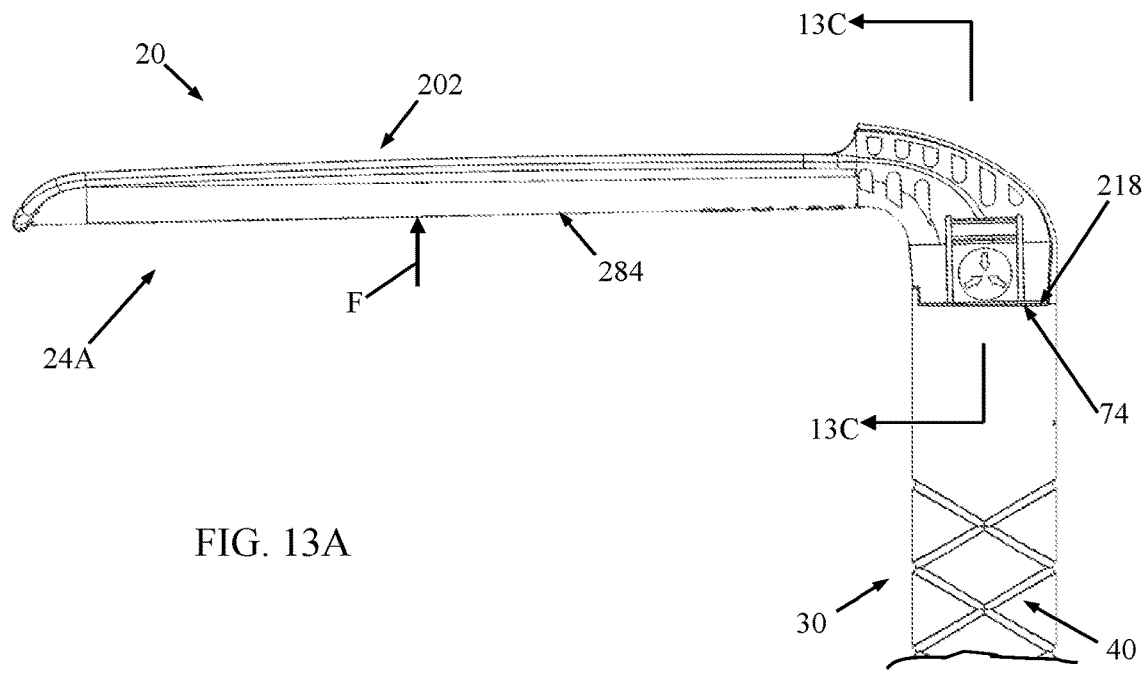
FIG. 13A is a side view of a portion of the modular surgical retractor of FIG. 1A upon final attachment of the blade to the handle assembly.
Figure 13B:
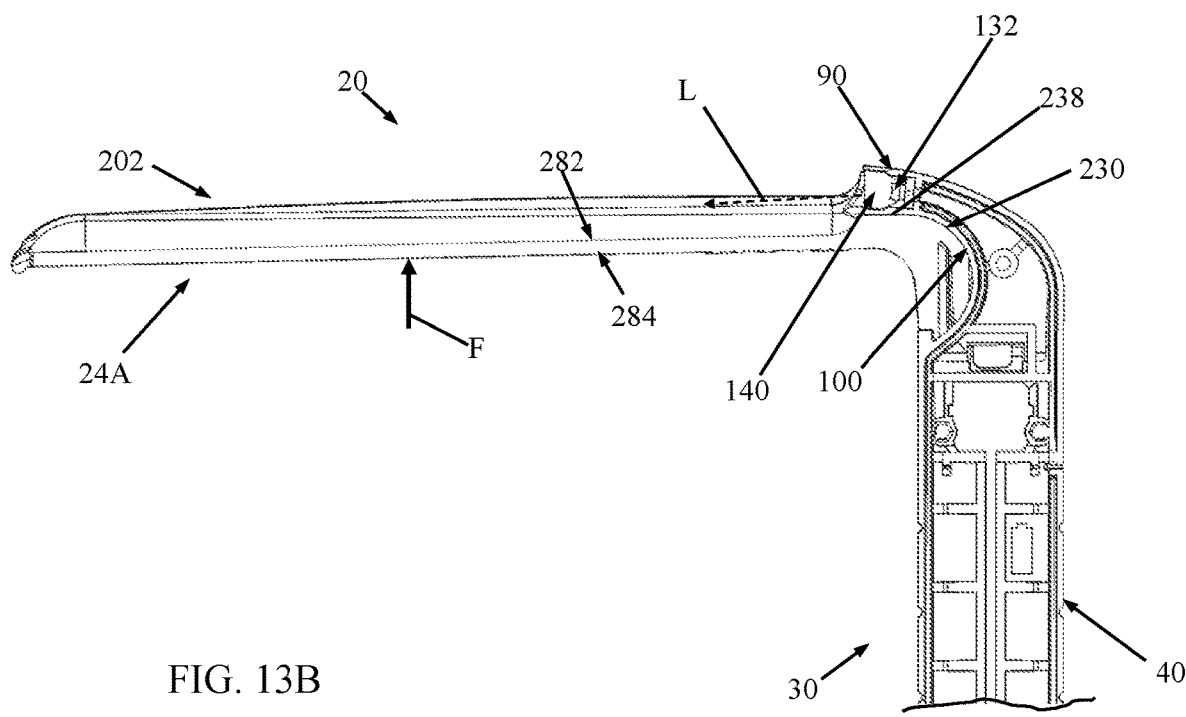
FIG. 13B is a longitudinal cross-sectional view of the arrangement of FIG. 13A.
Figure 13C:
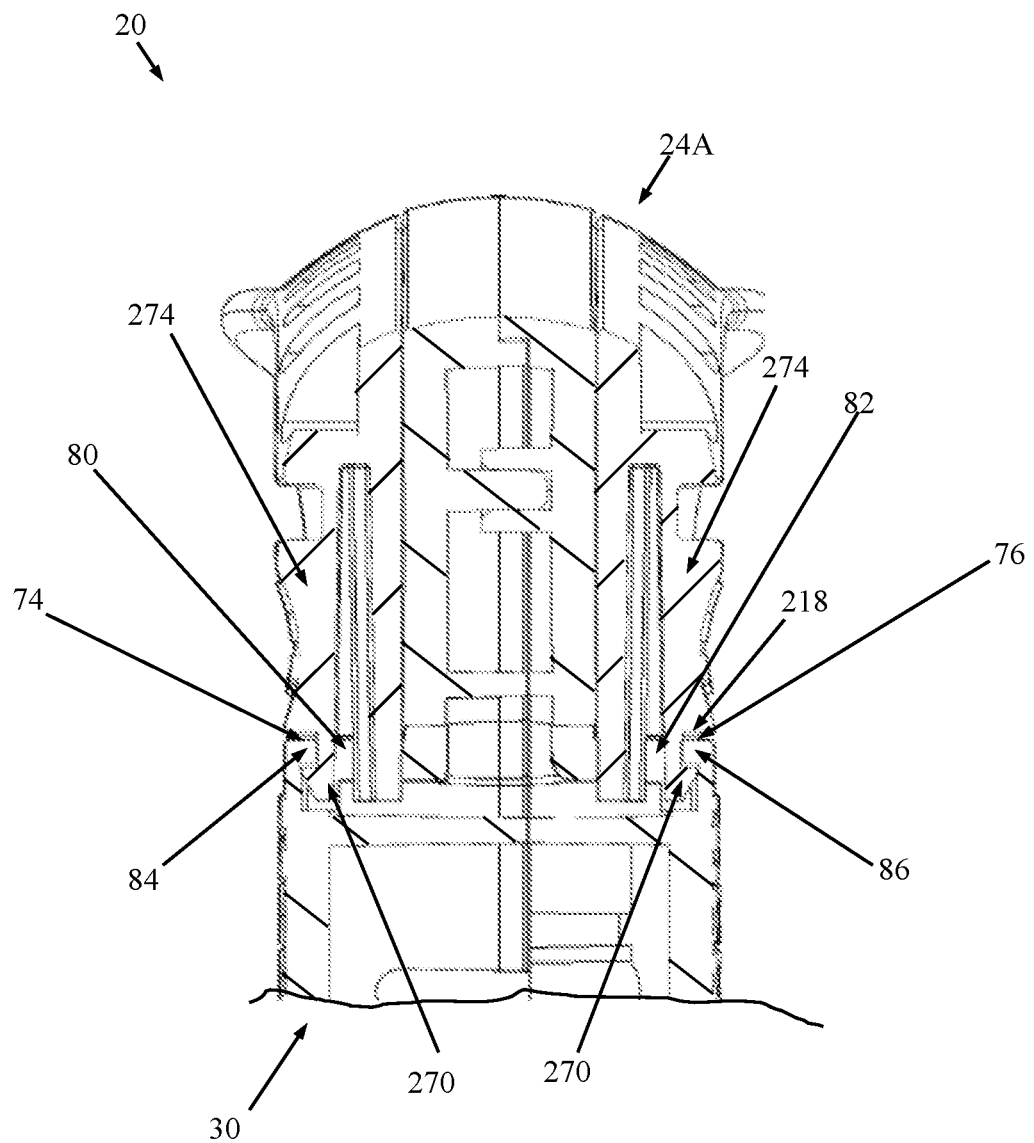
FIG. 13C is a cross-sectional view of a portion of the arrangement of FIG. 13A, taken along the line 13C-13C.

Final attachment between the blade 24A and the handle 30 is reflected by FIGS. 13A-13C. The attachment surface 218 contacts or abuts against the shoulder segments 74, 76, optionally with a flush interface. Similarly, the inside face 100 along the tail region 90 contacts or abuts against the contact segment 238 of the floor 230. As best shown in FIG. 13C, the clips 270 are received within a corresponding one of the notches 80, 82, and engage with a corresponding one of the interior ledges 84, 86. Finally, the latch 78 nests within the recess 246 (more clearly visible in FIG. 1A).

With continued reference to FIGS. 13A and 13B, once the blade 24A has been attached to the handle 30, the surgical retractor 20 can be utilized by a practitioner to perform various surgical retraction procedures as desired. The base 40 is appropriately sized for convenient handling by a single hand of the user. The blade member 202 extends at an approximately 90 degree angle relative to the base 40, and is thus conducive to many expected surgical retraction procedures performed by a user while gasping the base 40. With many surgical retraction procedures, the surgical retractor 20 will be employed to lift and/or push tissue. In many instances, a surgical retraction procedure includes locating the exterior surface 284 of the blade member 202 against tissue to be retracted, followed by the user applying a pulling force on to the handle 30 so as to retract the contacted tissue. The contacted tissue naturally resists the retraction force, effectively generates a tissue force F against the blade member 202 in response to the user-applied pulling force on the handle 30. The force F, in turn, creates a moment of the matched radius section of the blade 24A and the handle 30 in the same direction (e.g., at the interface between the neck inside face 100 and the floor 230). Under load, the blade 24A is held in a position normal to the handle 30 by contact between the attachment surface 218 of the blade 24A with the shoulder segments 74, 76 of the handle 30, and by contact between contact segment 238 of the floor 230 of the blade 24A with the inside face 100 of the handle 30 along the tail region 90. The tissue force F is thus dispersed through these contact areas and into the handle 30, creating a strong interface that facilitates use of the surgical retractor 20 in performing tissue retraction procedures requiring high tissue lifting forces.

Where desired, the light source 130 can be powered on as described above (e.g., via operation of the power delivery assembly 52 (FIG. 2)). As generally reflected by FIG. 13B, the lens body 140 directs light from the light source 132 along or in general alignment with the interior surface 282 of the blade member 202 (emitted light L is generally drawn in FIG. 13B).

Following use of the surgical retractor 20, the blade 24A can be removed from the handle 30. In this regard, and with reference to FIG. 13C, the tabs 274 are pressed inwardly, causing the corresponding clip 270 to disengage from the respective interior ledge 84, 86. The blade 24A can then be rotated relative to the handle 30 (and/or vice-versa) in a reverse manner to the attachment steps described above, thereby freeing the blade 24A from the handle 30.

Figure 14:
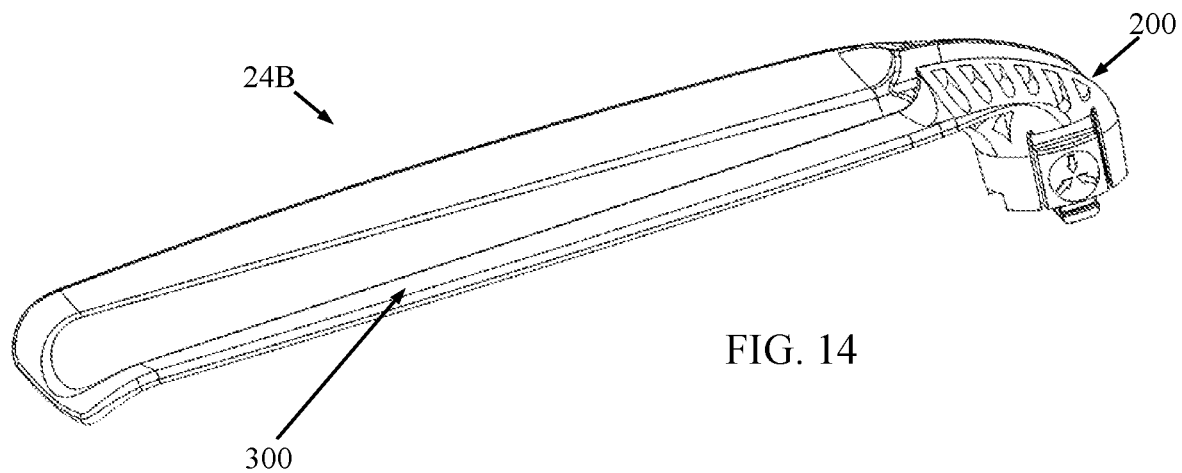
FIG. 14 is a perspective view of another blade useful with the modular surgical retractors of the present disclosure.
Figure 15:
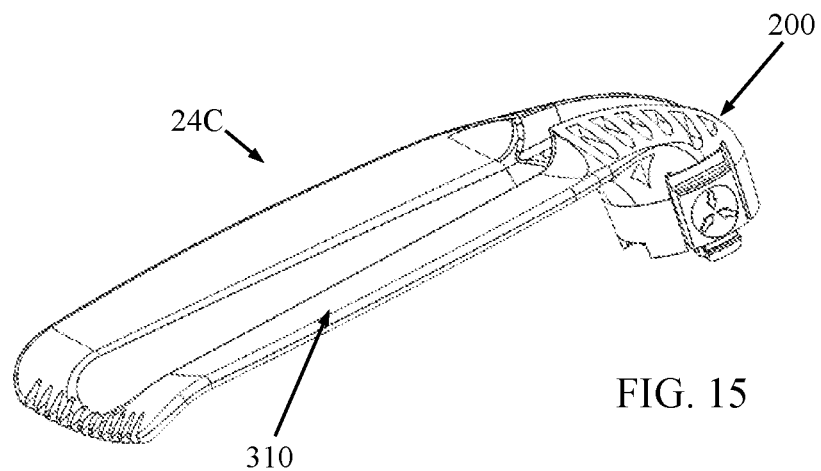
FIG. 15 is a perspective view of another blade useful with the modular surgical retractors of the present disclosure.
Figure 16:
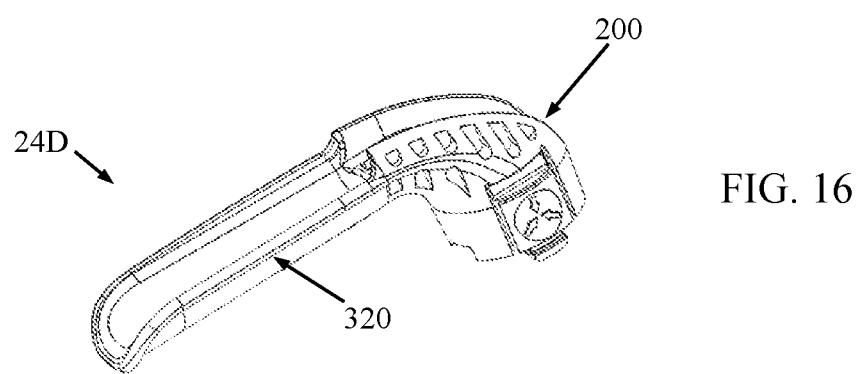
FIG. 16 is a perspective view of another blade useful with the modular surgical retractors of the present disclosure.

The blade 24A described above is but one example of a blade useful with the modular surgical retractors of the present disclosure. For example, another blade 24B useful with the modular surgical retractors of the present disclosure is shown in FIG. 14 and includes the head section 200 as described above and a blade member 300. A size and shape of the blade member 300 differs from that of the blade member 202 (FIG. 1B). However, by including the head section 200, the blade 24B is readily attached to and removed from the handle 30 (FIG. 1B) commensurate with the descriptions above. Similarly, another optional blade 24C in accordance with principles of the present disclosure is shown in FIG. 15 and includes the head section 200 and a blade member 310. FIG. 16 illustrates yet another optional blade 24D in accordance with principles of the present disclosure that includes the head section 200 and a blade member 320. In some embodiments, two or more or all of the blades 24A, 24B, 24C, 24D (and/or other blades that include the head section 200 and a differently-shaped blade member) can be provided to a clinician along with the handle assembly 22 (FIG. 1B) as part of a kit. Depending upon the particular surgical retraction procedure to be performed, the user can select the desired the blade, attach the selected blade to the handle assembly 22, and perform the procedure.

The modular surgical retractors of the present disclosure provide a marked improvement over previous designs. A variety of different blades are readily attached to and removed from an ergonomic handle, with a strong, robust interface being established between the blade and the handle when attached. Further, a light source is carried by the handle, located to emit light along an attached blade in a manner conducive to desired illumination of the surgical field.

Although the present disclosure has been described with reference to preferred embodiments, workers skilled in the art will recognize that changes can be made in form and detail without departing from the spirit and scope of the present disclosure. For example, while the modular surgical retractors have been described as including a light source carried by the handle, in other embodiments the modular surgical retractors of the present disclosure need not include a light source.

What is claimed is:

1. A modular surgical retractor comprising:
   a handle including:
      a base defining opposing, first and second ends,
      a neck projecting from the first end in a direction away from the second end to a tail region; and
   a first blade including:
      a head section including a first side wall, an opposing second side wall and a floor, wherein a surface of the floor is contiguous with, and extends between, a surface of the first side wall and a surface of the second side wall, and further wherein the surface of the first side wall, the surface of the second side wall, and the surface of the floor combine to define a slot sized to receive the neck,
      a blade member projecting from the head section;
   wherein the handle and the first blade are configured to provide an attached state in which the first blade is removably attached to the handle, the attached state including an attachment face of each of the side walls in contact with the first end, the neck nested between the first and second side walls, and the surface of the floor in contact with the tail region.

2. The modular surgical retractor of claim 1, wherein the retractor is configured such that in the assembled state, interface between the side walls and the first end and between the floor and the tail region resists a force applied to the blade member normal to a major plane of the blade member.

3. The modular surgical retractor of claim 1, wherein the first end defines first and second shoulder segments at opposite sides of the neck, and further wherein the attached state include the attachment face of the first side wall in contact with the first shoulder segment and the attachment face of the second side wall in contact with the second shoulder segment.

4. The modular surgical retractor of claim 1, wherein the base forms a first notch in the first end.

5. The modular surgical retractor of claim 4, wherein the head section further includes a first clip projecting from the attachment face of the first side wall, and further wherein the attached state includes the first clip nested within the first notch.

6. The modular surgical retractor of claim 5, wherein the base forms a second notch in the first end, the first and second notches being located at opposite sides of the neck, and further wherein the head section further includes a second clip projecting from the attachment face of the second side wall, and even further wherein the attached state includes the second clip nesting within the second notch.

7. The modular surgical retractor of claim 1, wherein the base has an elongated shape defining a longitudinal axis, and further wherein the tail region is off-set from the first end in both a longitudinal direction parallel with the longitudinal axis and a transverse direction perpendicular to the longitudinal axis.

8. The modular surgical retractor of claim 1, wherein the neck defines an inside face, an outside face opposite the inside face, and opposing side faces, and further wherein the attached state includes at least a portion of the inside face in contact with the floor.

9. The modular surgical retractor of claim 8, wherein at least a segment of the inside face is curved in extension from the first end to the tail region.

10. The modular surgical retractor of claim 9, wherein the floor defines a curvature substantially identical to a curvature of the inside face.

11. The modular surgical retractor of claim 9, wherein the inside face is substantially flat along the tail region, and further wherein the floor includes a substantially flat segment, and even further wherein the attached state includes the inside face of the tail region in contact with the substantially flat segment of the floor.

12. The modular surgical retractor of claim 1, further comprising:
   a light source disposed within the neck.

13. The modular surgical retractor of claim 12, wherein the light source is fixed to the neck.

14. The modular surgical retractor of claim 13, wherein the attached state includes light emitted from the light source being directed onto a face of the blade member.

15. The modular surgical retractor of claim 12, further comprising a lens disposed between light source and an open end of the tail region.

16. The modular surgical retractor of claim 12, wherein the light source is an LED.

17. The modular surgical retractor of claim 12, further comprising a power source disposed within the base.

18. The modular surgical retractor of claim 17, further comprising circuitry disposed within the base and configured to selectively electrically connect the power source with the light source.

19. The modular surgical retractor of claim 1, further comprising:
   a second blade including:
      a head section,
      a blade member projecting from the head section;

wherein the blade member of the second blade differs from the blade member of the first blade by at least one parameter selected from the group consisting of size and shape;

and further wherein the head section of the second blade and the head section of the first blade are identical.

20. A modular surgical retractor comprising:

a handle including:

a base defining opposing, first and second ends, a neck projecting from the first end to a tail region, wherein the base has an elongated shape defining a longitudinal axis, and further wherein the tail region is off-set from the first end in both a longitudinal direction parallel with the longitudinal axis and a transverse direction perpendicular to the longitudinal axis; and a first blade including:

a head section including a first side wall, an opposing second side wall and a floor, wherein a surface of the floor is contiguous with, and extends between, a surface of the first side wall and a surface of the second side wall, and further wherein the surface of the first side wall, the surface of the second side wall, and the surface of the floor combine to define a slot sized to receive the neck, a blade member projecting from the head section;

wherein the handle and the first blade are configured to provide an attached state in which the first blade is removably attached to the handle, the attached state including an attachment face of each of the side walls in contact with the first end, the neck nested between the first and second side walls, and the surface of the floor in contact with the tail region.

* * * * *